US011499194B2

(12) United States Patent
Finkel et al.

(10) Patent No.: US 11,499,194 B2
(45) Date of Patent: *Nov. 15, 2022

(54) CXR4 AS A SUSCEPTIBILITY LOCUS IN JUVENILE IDIOPATHIC ARTHRITIS (JIA) AND METHODS OF USE THEREOF FOR THE TREATMENT AND DIAGNOSIS OF THE SAME

(71) Applicant: The Children's Hospital of Philadelphia, Philadelphia, PA (US)

(72) Inventors: Terri H. Finkel, Orlando, FL (US); Haitao Zhang, Rockville, MD (US); Hakon Hakonarson, Malvern, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 125 days.

This patent is subject to a terminal disclaimer.

(21) Appl. No.: 16/413,664

(22) Filed: May 16, 2019

(65) Prior Publication Data
US 2019/0309366 A1  Oct. 10, 2019

Related U.S. Application Data

(60) Division of application No. 15/233,868, filed on Aug. 10, 2016, now Pat. No. 10,344,331, which is a continuation of application No. 13/893,224, filed on May 13, 2013, now abandoned, which is a continuation-in-part of application No. PCT/US2011/060430, filed on Nov. 11, 2011.

(60) Provisional application No. 61/412,775, filed on Nov. 11, 2010.

(51) Int. Cl.
*C12Q 1/6883* (2018.01)
*G01N 33/50* (2006.01)

(52) U.S. Cl.
CPC ....... *C12Q 1/6883* (2013.01); *G01N 33/5041* (2013.01); *G01N 33/5047* (2013.01); *C12Q 2600/118* (2013.01); *C12Q 2600/136* (2013.01); *C12Q 2600/156* (2013.01); *C12Q 2600/158* (2013.01); *G01N 2800/102* (2013.01)

(58) Field of Classification Search
None
See application file for complete search history.

(56) References Cited

U.S. PATENT DOCUMENTS 5,468,613 A * 11/1995 Erlich .............. C07K 14/70539
435/194
10,344,331 B2   7/2019 Finkel et al.

2007/0134690 A1   6/2007 Pascual et al.
2009/0029912 A1   1/2009 Gronthos et al.
2009/0298063 A1  12/2009 Kornman et al.

OTHER PUBLICATIONS

NCBI SNP Database for rs953387 (submission No. ss661397742, Sep. 6, 2000, available via URL: <ncbi.nlm.nih.gov/projects/SNP/snp_ss.cgi?subsnp_id=ss1397742> (Year: 2000).*
NCBI SNP Database for rs953387 (submission No. ss66822089, Nov. 9, 2006, available via URL: <ncbi.nlm.nih.gov/projects/SNP/snp_ss.cgi?subsnp_id=ss66822089> (Year: 2006).*
NCBI SNP Database for rs1123848, submission No. ss23708829, available via URL: <ncbi.nlm.nih.gov/projects/SNP/snp_ss.cgi?subsnp_id=ss23708829>, May 2004 (Year: 2004).*
NCBI SNP Database for rs4954564, submission No. ss75848556, available via URL: < ncbi.nlm.nih.gov/projects/SNP/snp_ss.cgi?subsnp_id=ss75848556>, Aug. 2007 (Year: 2007).*
NCBI SNP Database for rs1016269, submission No. ss66569306, available via URL: < ncbi.nlm.nih.gov/projects/SNP/snp_ss.cgi?subsnp_id=ss66569306>, Nov. 2006. (Year: 2006).*
Mcdowell, T.L., et al. "A genetic association between juvenile rheumatoid arthritis and a novel interleukin-1 alpha polymorphism." Arthritis Rheum. Feb. 1995;38(2):221-8.
NCBI publication "Cluster Report: rs953387." Sep. 6, 2000 [online]. [Retrieved on May 10, 2012]. Retrieved from the Internet<URL http://www.ncbi.nlm.nih.gov/projects/SNP/snp_ref.cgi?rs=953387>.
NCBI publication "IL1A interleukin 1, alpha [ *Homo sapiens* ]." Jul. 2008 [online]. [Retrieved on Feb. 23, 2012]. Retrieved from the internet <URL http://www.ncbi.nlm.nih.gov/gene/3552>.
ChemoCentryx "Preclnical Programs" available via url: < chemocentryx.com/product/preclinical_programs.html>, printed on Jul. 13, 2015.
Hattersley, Andrew T., and Mark I. McCarthy. "What makes a good genetic association study? " the Lancet 366.9493 (2005): 1315-1323.
Lucentini, Jack. "Gene association studies typically wrong: reproducible gene-disease associations are few and far between." The Scientist 18.24 (2004): 20-21.
Hirschhorn, Joel N., et al. "A comprehensive review of genetic association studies." Genetics in Medicine 4.2 (2002): 45-61.
Gagneux, Pascal, and Ajit Varki. "Genetic differences between humans and great apes." Molecular phylogenetics and evolution 18.1 (2001): 2-13.
Halushka, Marc K., et al. "Patterns of single-nucleotide polymorphisms in candidate genes for blood-pressure homeostasis." Nature Genetics 22.3 (1999): 239-247.
Mummidi, Srinivas, et al. "Evolution of human and non-human primate CC chemokine receptor 5 gene and mRNA Potential roles for haplotype and mRNA diversity, differential haplotype-specific transcriptional activity, and altered transcription factor binding to polymorphic nucleotides in the pathogenesis of HIV-1 and simian immunodeficiency virus." Journal of Biological Chemistry 275.25 (2000): 18946-18961.
NCBI dbSNP submission No. ss123008540, rs953387, available via URL: <ncbi.nlm.nih.gov/projects/SNP/snp_ss.cgi?subsnp_id=ss123008540> (Apr. 14, 2009).

(Continued)

*Primary Examiner* — Carla J Myers
(74) *Attorney, Agent, or Firm* — Kathleen D. Rigaut; Howson & Howson LLP

(57) ABSTRACT

Compositions and methods useful for the diagnosis and treatment of juvenile idiopathic arthritis are disclosed.

3 Claims, 9 Drawing Sheets

(56) References Cited

OTHER PUBLICATIONS

NCBI dbSNP submission No. ss121464468, rs1123848, available via URL: <ncbi.nlm.nih.gov/projects/SNP/snp_ss.cgi?subsnp_id=ss1214644682009.\> (Apr. 14, 2009).
Salman, Huda et al., "Plerixafor for autologous CD34+ cell mobilization", Core Evidence, 6:23-29 (2011).
Wei, Fangyuan et al., "Attentuation of osteoarthritis via blockade of the SDF-1/CXCR4 signaling pathway", Arthritis Research & Therapy, 4: 8177 (2012).

* cited by examiner

CXR4 AS A SUSCEPTIBILITY LOCUS IN JUVENILE IDIOPATHIC ARTHRITIS (JIA) AND METHODS OF USE THEREOF FOR THE TREATMENT AND DIAGNOSIS OF THE SAME

RELATED APPLICATIONS

This application is a divisional of U.S. patent application Ser. No. 15/233,868, filed Aug. 10, 2016, which is a continuation of U.S. patent application Ser. No. 13/893,224, filed May 13, 2013, which is a Continuation-In-Part of International Application No. PCT/US2011/60430 filed Nov. 11, 2011, which in turn claims the benefit of U.S. Provisional Application No. 61/412,775, filed Nov. 11, 2010. The entire contents of each of the foregoing applications is incorporated herein by reference as though set forth in full.

GOVERNMENT RIGHTS STATEMENT

This invention was made with government support under grant number AR058606 awarded by the National Institutes of Health. The government has certain rights in this invention.

FIELD OF THE INVENTION

This invention relates to the fields of genetics and the diagnosis of juvenile idiopathic arthritis (JIA). More specifically, the invention provides compositions and methods useful for the diagnosis and treatment of JIA.

BACKGROUND OF THE INVENTION

Several publications and patent documents are cited through the specification in order to describe the state of the art to which this invention pertains. Each of these citations is incorporated herein by reference as though set forth in full.

Pediatric arthritis is the leading cause of acquired disability in children, afflicting about one in 1000 children worldwide,[1] all ethnicities and both genders, with onset as early as the first year of life. Classification schemes for pediatric arthritis are under evolution, akin to the recent classification changes for adult rheumatoid arthritis;[2] juvenile rheumatoid arthritis (JRA) is the term used historically in North America, while juvenile idiopathic arthritis (JIA) is the preferred name elsewhere, and is now used increasingly worldwide. JIA is defined as a group of chronic arthritides of unknown etiology, occurring in children from 0 to 16 years of age.[3] Morbidity associated with JIA can be lifelong—with as many as 50% of children with JIA entering adulthood with active disease[1]—and represents a significant medical, financial, and emotional burden for patients, for their families, and for society. In the United States alone, arthritis and rheumatic diseases impact more than 46 million adults and 300,000 children, at a cost of S128 billion annually in direct and indirect medical costs. Multiple studies have shown that adults with JIA have lower rates of employment than matched controls, and health related quality of life is diminished in adults with JIA, particularly in those with active disease.[4] Prompt recognition of the disease is important in preventing permanent disability, however, lack of specific confirmatory testing often delays diagnosis. The optimal management of JIA remains complicated and poorly defined, despite recent advances in therapy[1]; important side effects of many of the newer therapeutic agents are increasingly being recognized, although associated risk factors for the development of these adverse events remain unknown.

The etiology of JIA is largely unknown. To our knowledge, there are no data supporting a major role for environmental exposures;[5] this does not preclude a role of the environment in the pathogenesis of JIA, but research to identify environmental risk factors is lacking. On the other hand, a genetic component has been implicated from twin and family studies:[6] monozygotic twins have a concordance rate between 25% and 40%; the calculated sibling recurrence risk ratio ($\lambda$s=15-30) is similar to that calculated for type I diabetes; sibling pairs tend to show concordance for age of onset, subtype and course; and a subset of patients with JIA exhibits a heritable predisposition to develop this disease with an autosomal dominant pattern of inheritance.

Yet, the genetic etiology of JIA remains elusive. JIA is an example of a complex phenotype that is likely to be determined by the net result of interactions between multiple genetic and environmental factors. Previous attempts at identifying the genetic basis of this disease through candidate gene studies have met with limited success. The major histocompatibility complex (MHC), in particular, the HLA-DRB1 locus, has been established as having the strongest influence on susceptibility to JIA,[7] contributing ~20% of the proportion of sibling recurrent risk.[8] Non-MHC loci are important as well, although candidate gene studies have only convincingly demonstrated associations for a few loci, and only four (PTPN22, STAT4, IL2-IL21, and IL2RA) have shown association in the same direction in two or more studies.[6,9-11] An inherent problem with candidate gene association studies is their reliance on a suspected disease-causing gene(s), whose identification derives from a particular biological hypothesis regarding pathogenesis of the disease or from previous work with related diseases. Since the pathophysiological mechanisms underlying JIA are unknown, continued use of the hypothesis-driven candidate gene association approach is likely to miss many important genetic risk factors for the disease. In view of all the foregoing it is clear a need exists to further characterize and elucidate the genetic and molecular mechanisms underlying this devastating disease.

SUMMARY OF THE INVENTION

In accordance with the present invention, methods are provided for the diagnosis and treatment of JIA. An exemplary method entails detecting the presence of at least one, two, three, four, five, six or all of the JIA associated CXCR4 SNPs or mutations in a target polynucleotide wherein if said (s) is/are present, said patient has an increased risk for developing JIA.

In one aspect of the present invention, a method for detecting a propensity for developing juvenile idiopathic arthritis (JIA) in a patient in need thereof is provided. An exemplary method entails detecting the presence of at least one SNP containing nucleic acid in a target polynucleotide, said SNP being informative of a the presence of an JIA associated alteration in the CXCR4 gene wherein if said SNP is present, said patient has an increased risk for developing JIA, wherein said SNP containing nucleic acid is provided in Table 4.

In another embodiment of the invention a method for identifying agents which alter immune cell function or signaling is provided. Such a method comprises providing cells expressing at least one nucleic acid comprising the JIA CXCR4 SNPs of the invention, (step a); providing cells which express the cognate wild type sequences which lack the SNP (step b); contacting the cells from each sample with a test agent and analyzing whether said agent alters immune signaling or function of cells of step a) relative to those of step b), thereby identifying agents which alter immune cell signaling or function. Methods of treating JIA patients via administration of test agents identified using the methods described herein are also encompassed by the present invention.

The invention also provides at least one isolated JIA related SNP-containing nucleic acid selected from the group listed in Table 4 and includes any SNP in linkage disequilibrium (LD) with these SNPs. In one embodiment, a multiplex SNP panel containing all of the informative SNPs from the tables provided herein and any of their LD associated SNPs is disclosed. Such SNP containing nucleic acids which indicate the presence of JIA associated nucleic acids may optionally be contained in a suitable expression vector for expression in immune cells. Alternatively, they may be immobilized on a solid support. In yet another alternative, the panel may be provided in silico.

According to yet another aspect of the present invention, there is provided a method of treating JIA in a patient determined to have at least one prescribed single nucleotide polymorphism indicative of the presence of an JIA, as described hereinbelow, by administering to the patient a therapeutically effective amount of at least one member of the agents listed in Table 12. This method provides a test and treat paradigm, whereby a patient's genetic profile is used to personalize treatment with therapeutics targeted towards specific immunological defects found in individuals exhibiting JIA. Such a test and treat model may benefit up to 50% of patients with JIA with greater efficacy and fewer side effects than non-personalized treatment.

The figure shows pairwise $r^2$ LD values of the top 10 SNPs from the HapMap CEU population (URLs). The CXCR4 gene is drawn to scale in relation to the associated SNPs.

Figure 4:
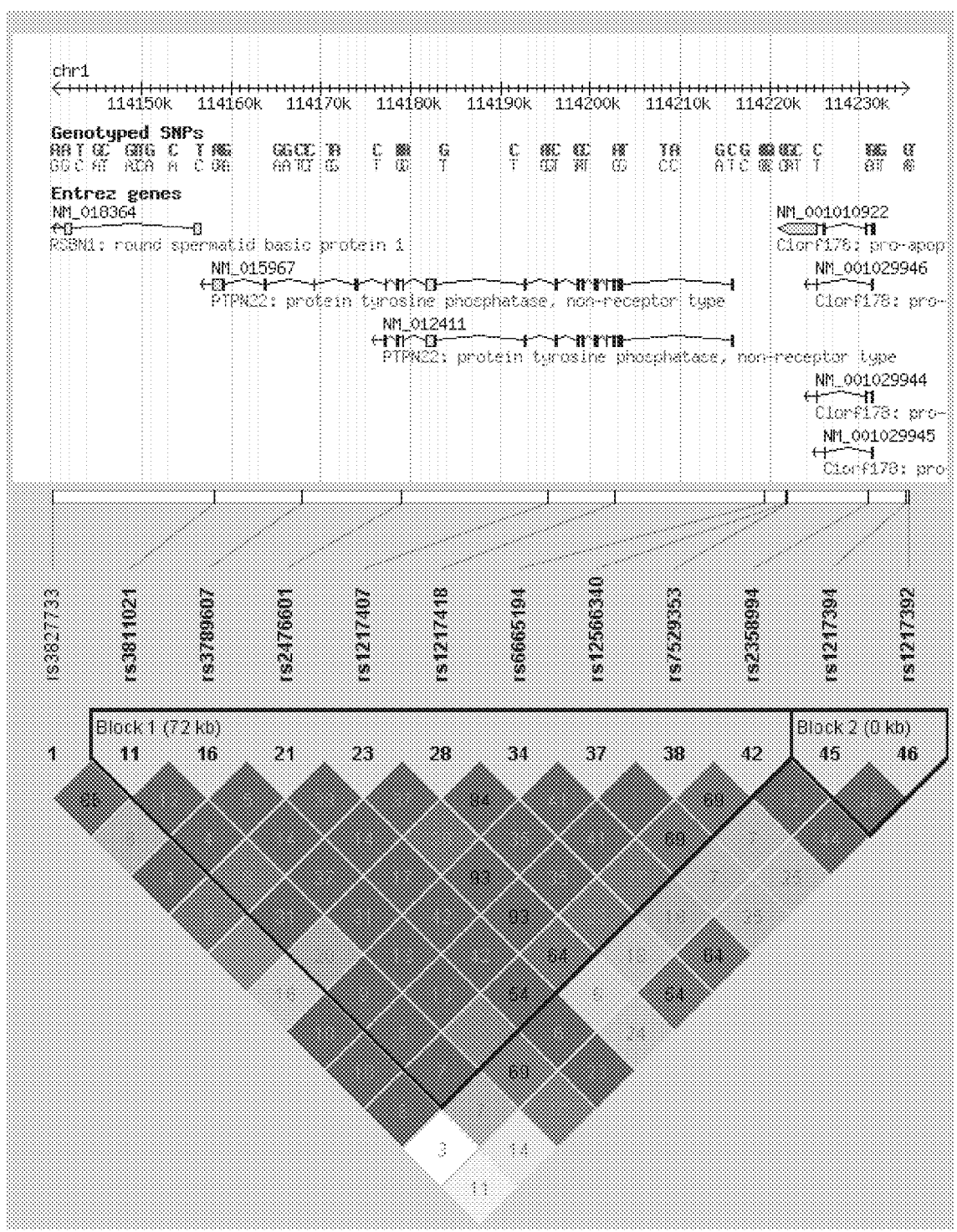

FIG. 4. Representation of the PTPN22 linkage-disequilibrium (LD) blocks. The figure shows pairwise $r^2$ LD values from the HapMap CEU population. The PTPN22 gene is drawn to scale in relation to the associated SNPs.

Figure 5:
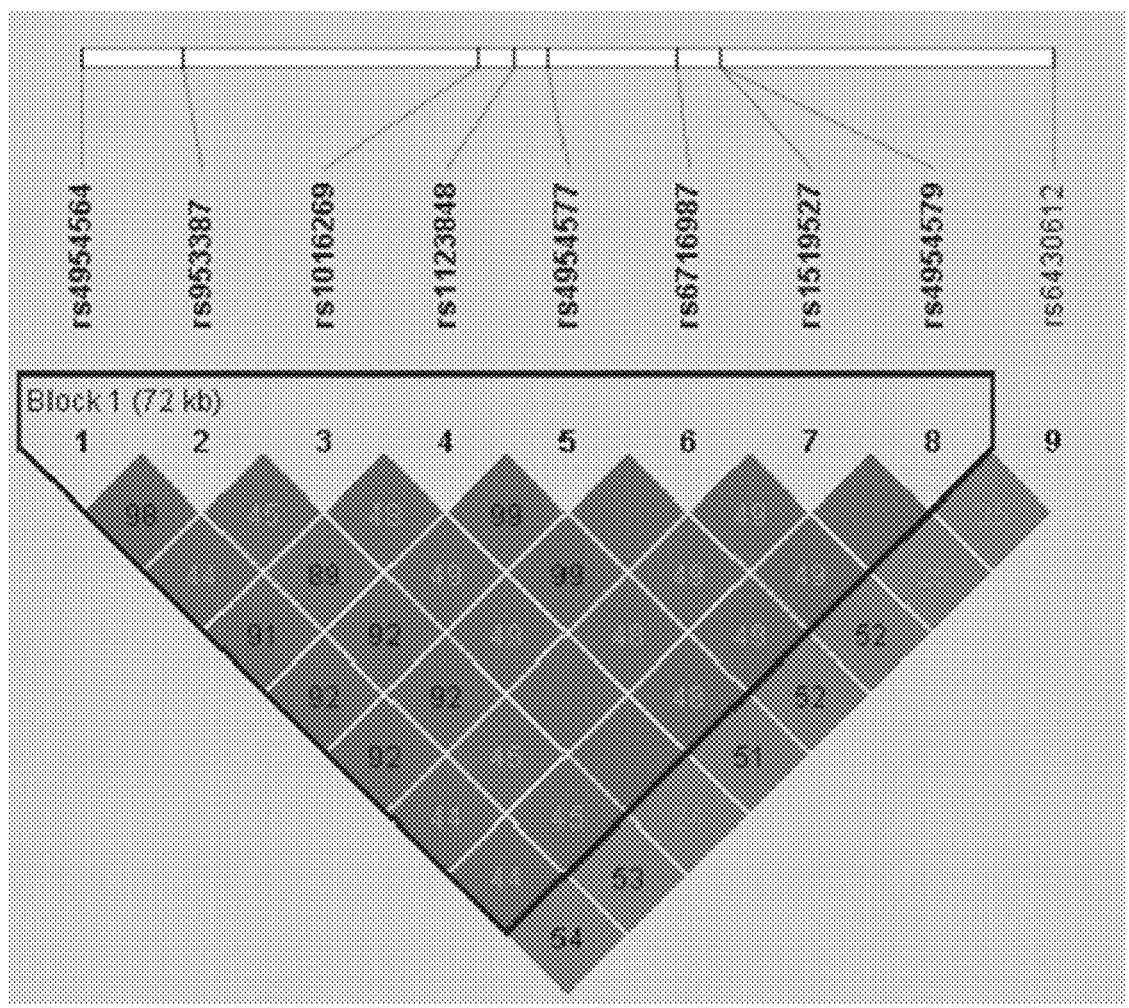

FIG. 5. The most significantly associated genotyped and imputed SNPs ($p<5\times10^{-8}$ in the combined meta-analysis) in the vicinity of CXCR4 on chromosome 2q21.

Figure 6:
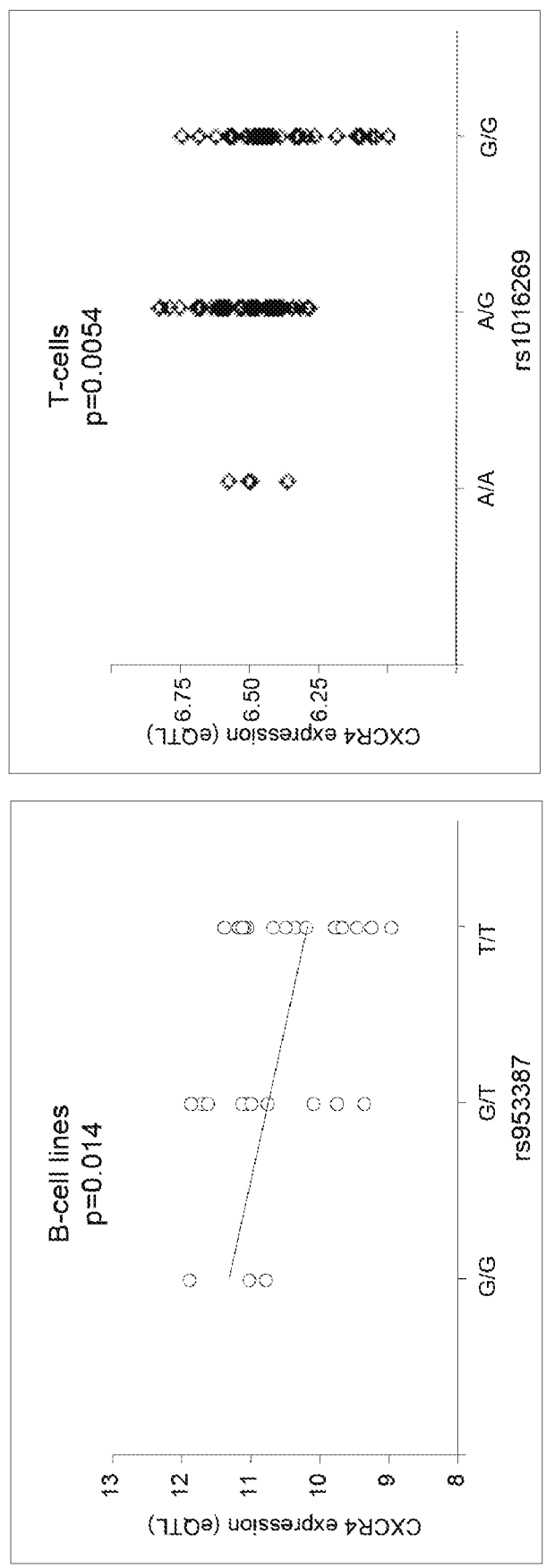

FIG. 6. CXCR4 expression levels stratified by SNP genotype.

The SNP genotypes of rs953387 and rs1016269 are associated with CXCR4 transcript levels by quantitative PCR (eQTL) in immortalized B-cell lines (from 30 CEU children) and T-cells (from umbilical cords of 75 individuals of Western European origin), respectively.

Figure 7:
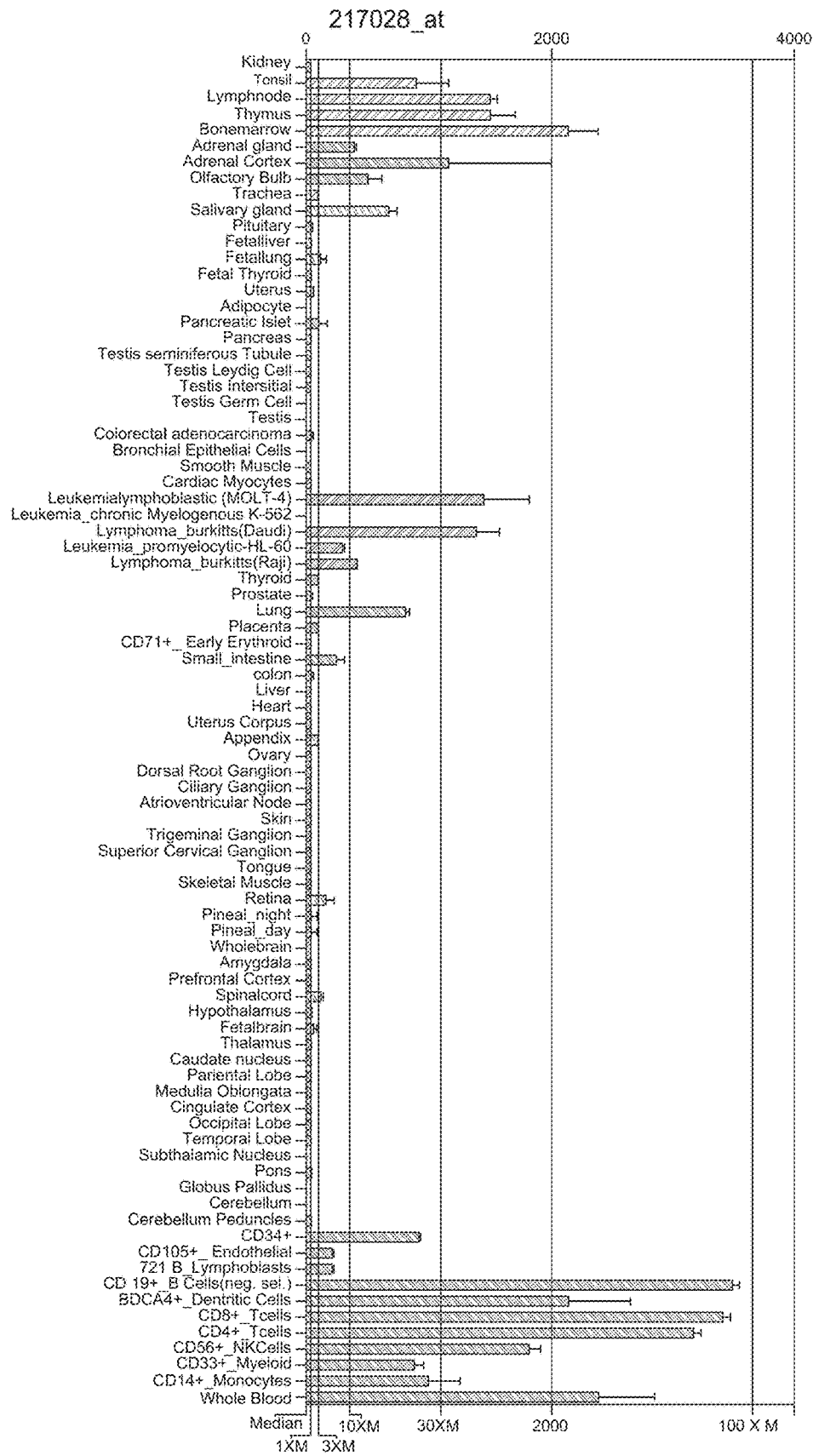
Figure 7:
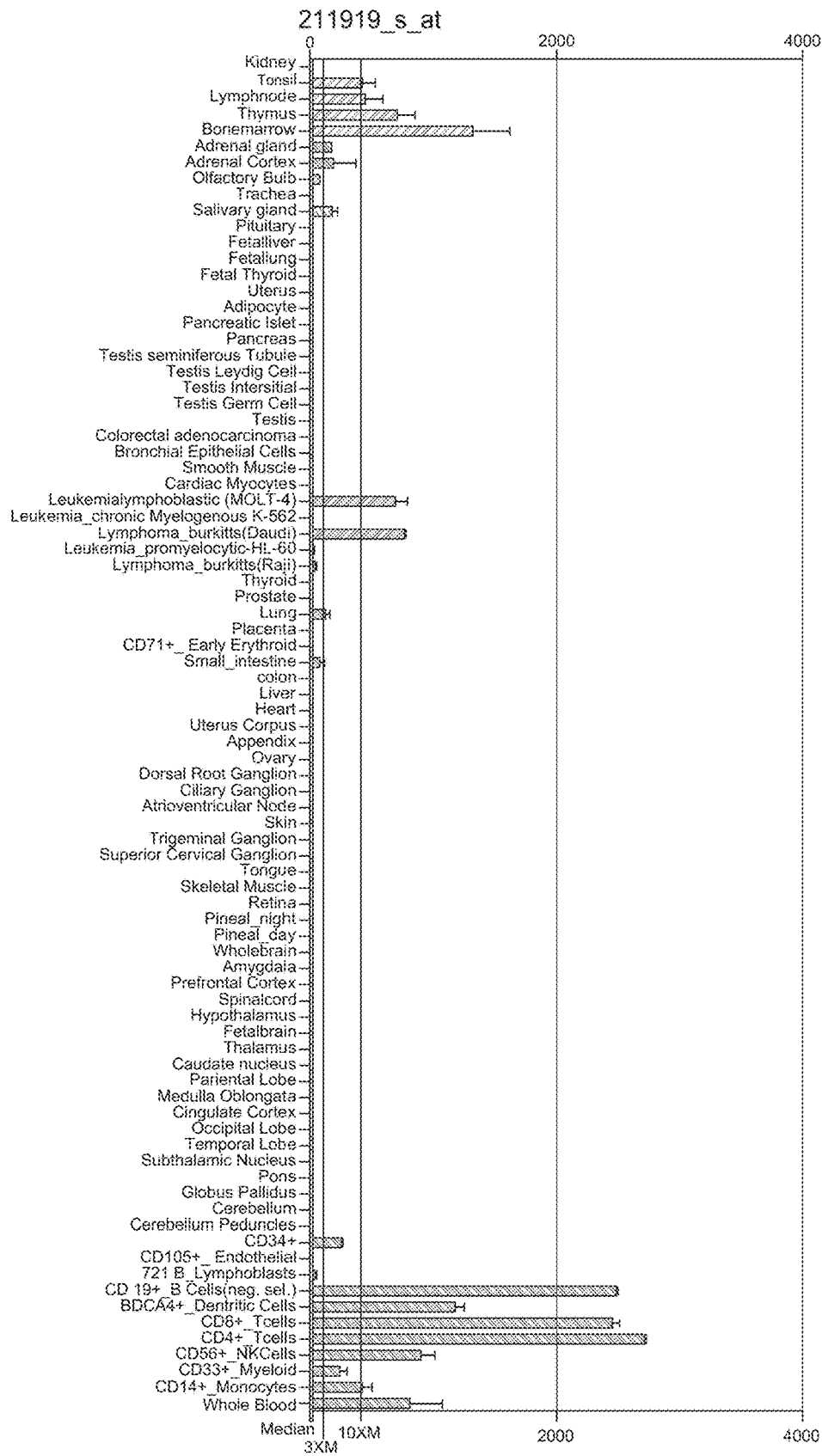
Figure 7:
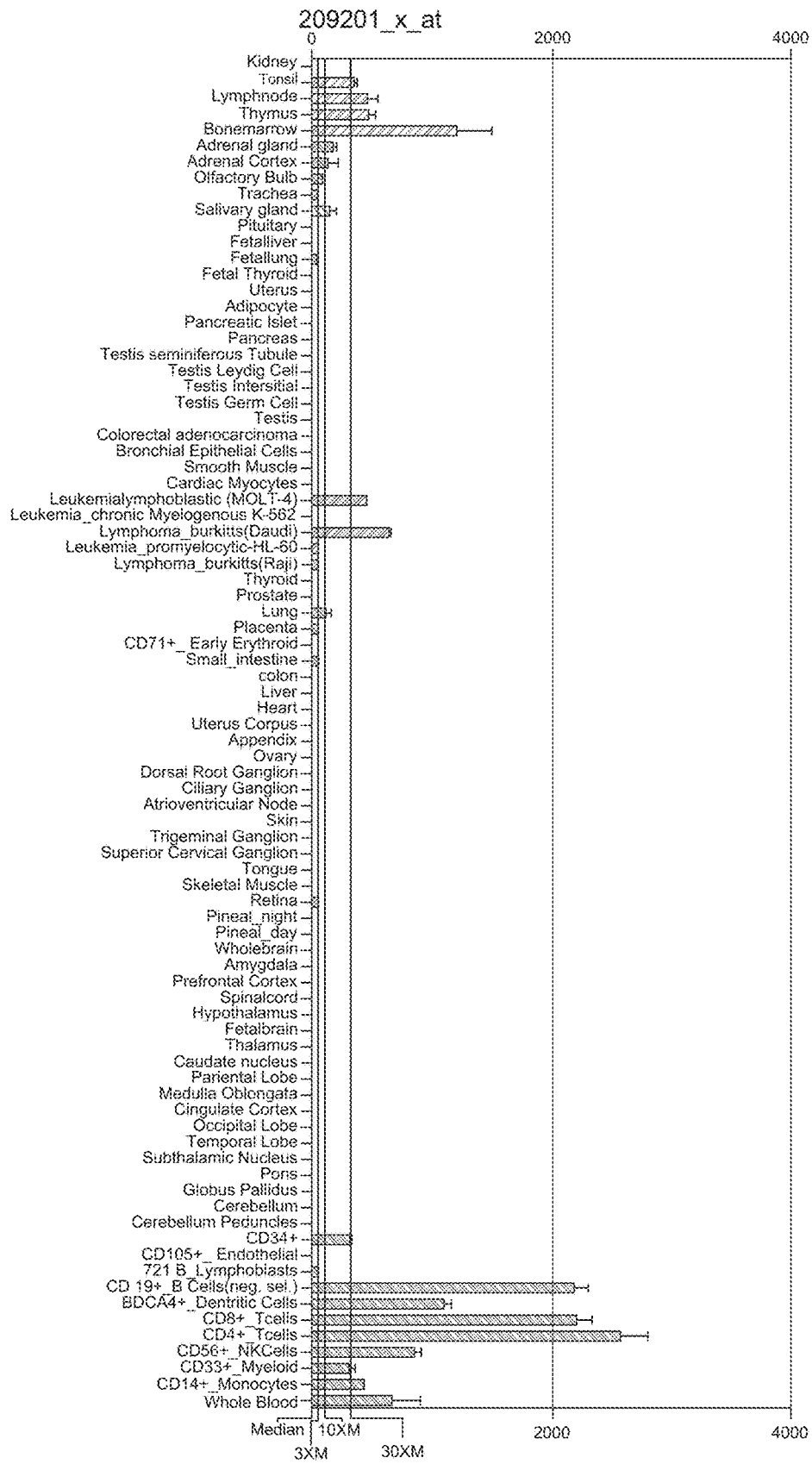

FIG. 7. CXCR4 tissue-specific gene expression levels (probe identifiers: 217028_at, 211919_s_at, and 209201_x_at), based on the GNF SymAtlas database on 79 human tissues. Expression of CXCR4 is most prominent in the CD-annotated T-cells, B-cells, NK and dendritic cells.

DETAILED DESCRIPTION OF THE INVENTION

The genome-wide association approach serves the critical need for a more comprehensive and unbiased strategy to identify causal genes related to JIA. We have assembled a large cohort of JIA patients—'large', given the relatively low prevalence of JIA—for a genome-wide association study (GWAS), which requires no a priori assumptions regarding pathology. We have taken a novel approach to discovery of JIA susceptibility loci by focusing on the phenotypic commonality amongst our patients, that is, chronic inflammation of the joints. We report a GWAS of JIA designed to address the hypothesis that clinically different phenotypes share common susceptibility loci, which confer a risk in childhood for inflammatory arthritis. This approach is supported by the intriguing discovery of common disease susceptibility loci across multiple autoimmune diseases.[9,12,13]

To identify risk factors underlying JIA, we performed a genome-wide association study and replication in 1166 JIA cases and 9500 unrelated controls of European ancestry. Two epidemiological JIA cohorts were combined and designated as the discovery cohort and three as de novo independent replication cohorts. Variants at the CXCR4 locus on 2q21 reached genome-wide significance in the discovery cohort for association with JIA, and were confirmed in our independent replication cohorts (combined $p=1.03\times10^{-13}$ for rs953387, near CXCR4). Participants with the minor allelic variant of rs953387 (OR 0.59, 95% CI 0.50-0.69) and with associated variants in close linkage disequilibrium with the rs953387 minor allele were protected from JIA, with about two-fold lower risk of JIA than non-carriers. CXCR4 expression was correlated with the genotype of rs953387 in lymphoblastoid cell lines (p=0.014) and T-cells (p=0.0054). This is the first GWAS of JIA to discover a genome-wide significant susceptibility locus outside of the major histocompatibility complex (MHC), and the first genetic evidence implicating CXCR4 in the pathogenesis of autoimmune disease. This cell-surface chemokine receptor has already been targeted in other diseases and may serve as a tractable therapeutic target for this crippling pediatric arthritis.

I. Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome.

"JIA-associated SNP" or "JIA-associated specific marker" is a SNP or marker which is associated with an increased or decreased risk of developing JIA not found normal patients who do not have this disease. Such markers may include but are not limited to nucleic acids, proteins encoded thereby, or other small molecules. Thus, the phrase "JIA-associated SNP containing nucleic acid" is encompassed by the above description.

"CXCR-4" is an alpha-chemokine receptor specific for stromal-derived-factor-1 (SDF-1 also called CXCL12), a molecule possessing potent chemotactic activity for lymphocytes. This receptor is one of several chemokine receptors that HIV isolates can use to infect CD4+ T cells. CXCR4 is upregulated during the implantation window in natural and hormone replacement therapy cycles in the endometrium, producing, in presence of a human blastocyst, a surface polarization of the CXCR4 receptors suggesting that this receptor is implicated in the adhesion phase of human implantation. CXCR4's ligand SDF-1 is known to be important in hematopoietic stem cell homing to the bone marrow and in hematopoietic stem cell quiescence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with JIA. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any JIA specific marker gene or nucleic acid, but does not hybridize to other nucleotides. Also polynucleotide which "specifically hybridizes" may hybridize only to a single specific marker, such as an JIA-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m=81.5"C+16.6 \text{ Log } [Na+]+0.41(\% G+C)-0.63(\% \text{ formamide})-600/\#bp \text{ in duplex}$$

As an illustration of the above formula, using [Na+]=[0.368] and 50% formamide, with GC content of 42% and an average probe size of 200 bases, the $T_m$ is 57"C. The $T_m$ of a DNA duplex decreases by 1-1.5"C with every 1% decrease in homology. Thus, targets with greater than about 75% sequence identity would be observed using a hybridization temperature of 42"C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the JIA specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the JIA specific marker nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism", or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably a JIA specific marker molecule, such as a marker described hereinbelow. Samples may include but are not limited to cells, body fluids, including blood, serum, plasma, cerebral spinal fluid, urine, synovial fluid, saliva, tears, pleural fluid and the like.

The terms "agent" and "compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the CNV or SNP-containing nucleic acids described herein or their encoded proteins. Agents and compounds may also be referred to as "test agents" or "test compounds" which are evaluated for potential biological activity by inclusion in screening assays described hereinbelow.

The term "modulate" as used herein refers to increasing/promoting or decreasing/inhibiting a particular cellular, biological or signaling function associated with the normal activities of the genetic alteration containing molecules described herein or the proteins encoded thereby. For example, the term modulate refers to the ability of a test compound or test agent to interfere with signaling or activity of a gene or protein of the present invention. Alternatively, the term may refer to augmentation of the activity of such a protein.

II. Methods of Using JIA-Associated CXCR4 SNPs for Diagnosing a Propensity for the Development of JIA JIA-related SNP-containing CXCR4 nucleic acids, including but not limited to those listed below may be used for a variety of purposes in accordance with the present invention.

JIA-associated SNP-containing DNA, RNA, or fragments thereof may be used as probes to detect the presence of and/or expression of JIA specific markers. Methods in which JIA specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting JIA-associated SNPs may be conducted on any type of biological sample, including but not limited to body fluids (including synovial fluid, blood, urine, serum, gastric lavage, cerebral spinal fluid), any type of cell (such as brain cells, white blood cells, mononuclear cells, fetal cells in maternal circulation) or body tissue.

Clearly, JIA-associated SNP-containing nucleic acids, vectors expressing the same, JIA SNP-containing marker proteins and anti-JIA specific marker antibodies of the invention can be used to detect JIA associated SNPs in body tissue, cells, or fluid, and alter JIA SNP-containing CXCR4 marker protein expression for purposes of assessing the genetic and protein interactions involved in the development of JIA.

In most embodiments for screening for JIA-associated SNPs, the JIA-associated SNP-containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are important in the art.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

In another embodiment, the sequence information for the CXCR4 SNPs associated with JIA of the invention are stored in a computer readable medium and the patients genetic information has already been obtained and is also stored in a computer readable medium. In this embodiment, the diagnostic method entails a comparison of this control and patient sequence information in silico in order to diagnose an increased risk for developing JIA.

Any of the aforementioned techniques may be used to detect or quantify JIA-associated SNP marker expression and accordingly, diagnose an increased risk for developing the same.

III. Kits and Articles of Manufacture

Any of the aforementioned products can be incorporated into a kit which may contain a JIA-associated SNP specific CXCR4 marker polynucleotide or one or more such markers immobilized on a Gene Chip, an oligonucleotide, a polypeptide, a peptide, an antibody, a label, marker, reporter, a pharmaceutically acceptable carrier, a physiologically acceptable carrier, instructions for use, a container, a vessel for administration, an assay substrate, or any combination thereof.

IV. Methods of Using JIA-Associated CXCR4 SNPs for the Development of Therapeutic Agents Since the SNPs identified herein have been associated with the etiology of JIA, methods for identifying agents that modulate the activity of the CXCR4 gene and its encoded products containing such SNPs should result in the generation of efficacious therapeutic agents for the treatment of this disorder.

The CXCR4 locus provides a suitable target for the rational design of therapeutic agents. Small nucleic acid molecules or peptide molecules corresponding to these regions may be used to advantage in the design of therapeutic agents that effectively modulate the activity of the encoded proteins.

Molecular modeling should facilitate the identification of specific organic molecules with capacity to bind to the active site of the proteins encoded by the SNP-containing nucleic acids based on conformation or key amino acid residues required for function. A combinatorial chemistry approach will be used to identify molecules with greatest activity and then iterations of these molecules will be developed for further cycles of screening. Molecules available for testing in this screening assay, include without limitation, those provided in Table 12. Table 12 provides suitable drug candidates, their commercial sources and reported mechanisms of action.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered JIA CXCR4 gene. These host cell lines or cells are defective at the polypeptide level. The host cell lines or cells are grown in the presence of drug compound. Altered immune signaling or function of the host cells is measured to determine if the compound is capable of regulating this function in the defective cells. Host cells contemplated for use in the present invention include but are not limited to bacterial cells, fungal cells, insect cells, mammalian cells, and plant cells. However, mammalian cells, particularly immune cells are preferred. The JIA-associated SNP encoding CXCR4 DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in Saccharomyces are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/ V5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and Saccharomyces promoters such as the gal4 inducible promoter and the PGK constitutive promoter may also be employed.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the JIA-associated CXCR4 SNPs of the present invention or functional fragments thereof provide a system in which to screen potential compounds or agents for the ability to modulate the development of JIA. Thus, in one embodiment, the nucleic acid molecules of the invention may be used to create recombinant cell lines for use in assays to identify agents which modulate aspects of cellular metabolism associated with JIA and aberrant immune cell function. Also provided herein are methods to screen for compounds capable of modulating the function of proteins encoded by CXCR4 SNP-containing nucleic acids.

Another approach entails the use of phage display libraries engineered to express fragment of the polypeptides encoded by the SNP-containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21 It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of SNP-containing CXCR4 nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of JIA-associated CXCR4 SNP-containing nucleic acids enables the production of strains of laboratory mice carrying the JIA-associated SNPs containing nucleic acid of the invention. Transgenic mice expressing the JIA-associated SNP(s) of the invention provide a model system in which to examine the role of the SNP containing CXCR4 nucleic acids play in the development and progression towards JIA. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that CXCR4 protein plays in various cellular metabolic processes, including: aberrant immune signaling molecule production and function. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of JIA-associated SNP-containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated JIA-associated SNP CXCR4 genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing JIA-associated SNP-containing nucleic acid as a targeted insertional cassette provides means to detect a successful insertion as visualized, for example, by acquisition of immunoreactivity to an antibody immunologically specific for the CXCR4 polypeptide encoded by JIA-associated SNP nucleic acid and, therefore, facilitates screening/selection of ES cells with the desired genotype.

As used herein, a knock-in animal is one in which the endogenous murine gene, for example, has been replaced with human JIA-associated CXCR4 SNP-containing gene of the invention. Such knock-in animals provide an ideal model system for studying the development of JIA.

As used herein, the expression of a JIA-associated SNP-containing nucleic acid, a JIA-associated CXCR4 fusion protein in which the SNP is encoded can be targeted in a "tissue specific manner" or "cell type specific manner" using a vector in which nucleic acid sequences encoding all or a portion of an JIA-associated SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

Methods of use for the transgenic mice of the invention are also provided herein. Transgenic mice into which a nucleic acid containing the JIA-associated SNP or its encoded CXCR4 protein have been introduced are useful, for example, to develop screening methods to screen therapeutic agents to identify those capable of modulating the development of JIA.

V. Pharmaceutical and Peptide Therapies

The elucidation of the role played by the JIA associated CXCR4 SNPs described herein in immune cell signaling and function facilitates the development of pharmaceutical compositions useful for treatment and diagnosis of JIA. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following materials and methods are provided to facilitate the practice of the present invention.

Subjects and Methods
Participants

We undertook a multicenter, genome-wide association study of five epidemiological cohorts in the USA, Australia, and Norway (Table 1). Our case cohorts were comprised of patients with JIA, with onset of arthritis at <16 years of age. JIA diagnosis and JIA subtype were determined according to the International League of Associations for Rheumatology (ILAR) revised criteria[3] and confirmed using the JIA Calculator™ software (URLs),[14] an algorithm-based tool adapted from the ILAR criteria. A summary of design and clinical characteristics for our study samples is shown in Tables 1-3.

TABLE 1

Discovery and replication cohorts.
The JIA data set following standard quality control procedures and exclusion of non-European ancestry is shown.

| JIA Data Set[a] | Purpose | Cases | Controls | Total |
|---|---|---|---|---|
| TSRHC + CMHC | Discovery | 388 | 2500 | 2888 |
| CHOP | Replication 1 | 182 | 2000 | 2182 |
| MCRI | Replication 2 | 154 | 2000 | 2154 |
| OUH | Replication 3 | 442 | 3000[b] | 3442 |
| Combined | Meta-analysis | 1166 | 9500 | 10,666 |

[a]JIA Data Set: TSRHC; Texas Scottish Rite Hospital for Children, Dallas, Texas, USA; CMHC; Children's Mercy Hospitals and Clinics, Kansas City, Missouri, USA; CHOP; The Children's Hospital of Philadelphia, Philadelphia, Pennsylvania, USA; MCRI; Murdoch Childrens Research Institute, Melbourne, Australia; OUH; Department of Rheumatology, Oslo University Hospital, Rikshospitalet, Oslo, Norway.
[b]Out-of-study controls provided by the Wellcome Trust Case-Control Consortium.

TABLE 2

JIA subtypes in the study cohorts.

| JIA Subtypes[a] | Discovery[b] (TSRHC + CMHC) | Replication 1 (CHOP) | Replication 2 (MCRI) | Replication 3 (OUH) | CCHMC[c] | Total |
|---|---|---|---|---|---|---|
| Oligoarthritis, persistent + extended | 135 | 45 | 76 | 181 | — | 437 |
| Polyarthritis, RF negative | 86 | 35 | 40 | 88 | — | 249 |
| Oligoarthritis + Polyarthritis, RF negative | 221 | 80 | 116 | 269 | 814 | 1500 |
| Polyarthritis, RF positive | 19 | 7 | 10 | 18 | — | 54 |
| Polyarthritis, RF unknown | 27 | 0 | 0 | 0 | — | 27 |
| Systemic arthritis | 44 | 23 | 12 | 24 | — | 103 |
| Enthesitis-related arthritis | 38 | 32 | 6 | 62 | — | 138 |
| Psoriatic arthritis | 32 | 19 | 5 | 31 | — | 87 |
| Undifferentiated arthritis | 7 | 21 | 5 | 38 | — | 71 |
| Total | 388 | 182 | 154 | 442 | 814 | 1980 |

[a]Revised ILAR criteria.[1] For this study, a patient was considered to be rheumatoid factor (RF)-negative based on a single test; patients for whom the RF was indeterminant (27 patients) were excluded from subtype analysis.
[b]JIA Data Set: TSRHC; Texas Scottish Rite Hospital for Children, Dallas, Texas, USA; CMHC; Children's Mercy Hospitals and Clinics, Kansas City, Missouri, USA; CHOP; The Children's Hospital of Philadelphia, Philadelphia, Pennsylvania, USA; MCRI; Murdoch Childrens Research Institute, Melbourne, Australia; OUH; Department of Rheumatology, Oslo University Hospital, Rikshospitalet, Oslo, Norway.
[c]CCHMC, Cincinnati Children's Hospital Medical Center; controls for this dataset were comprised of 649 local and 2400 out-of-study controls (see Methods); proxy SNPs of the two JIA subtypes from CCHMC were not included in the meta-analysis (Table 2).

TABLE 3

Demographic characterization of the discovery and replication cohorts. The age at onset, gender, and subtype distributions of all case cohorts are similar to those reported previously for JIA.[1]

| JIA Subtypes[a] | % female | Age (years)[b] |
|---|---|---|
| Oligoarthritis, persistent | 73% | 5.9 (2.9, 9.7) |
| Oligoarthritis, extended | 82% | 3.95 (2.4, 7.8) |
| Polyarthritis, RF negative | 79% | 7.48 (3.2, 11.3) |
| Polyarthritis, RF positive | 95% | 13.5 (10.3, 15.1) |
| Systemic arthritis | 67% | 6.6 (3.2, 11.1) |
| Enthesitis-related arthritis | 40% | 11.9 (9.0, 14.1) |
| Psoriatic arthritis | 71% | 9.9 (7.0, 13.2) |
| Undifferentiated arthritis | 55% | 9.8 (4.5, 13.8) |
| Total | 68% | 8.3 (3.8, 12.2) |

[a]Revised ILAR criteria.
[1]For this study, a patient was considered to be rheumatoid factor (RF)-negative based on a single test; patients for whom the RF was indeterminant (27 patients) were excluded from subtype analysis.
[b]Age (years): median (25% percentile, 75% percentile)

The targeted discovery cohort prior to standard quality control (QC) procedures and exclusion of non-European ancestry was comprised of 464 subjects with JIA from Texas Scottish Rite Hospital for Children (TSRHC; Dallas, Tex.) and Children's Mercy Hospitals and Clinics (CMHC; Kansas City, Mo.) of self-reported European ancestry. To attempt to replicate associations in the discovery cohort, three independent case sample collections of JIA patients, also of self-reported European ancestry, were studied. One of the replication cohorts was comprised of 196 subjects from the Children's Hospital of Philadelphia (CHOP; Philadelphia, Pa.). A second independent replication cohort was comprised of 221 subjects from the Murdoch Childrens Research Institute (MCRI; Royal Children's Hospital, Melbourne, Australia). A third independent replication cohort was comprised of 504 subjects from Oslo University Hospital (OUH; Oslo, Norway). A subset of subjects from these sites has been described previously.[12,15,16,17] The clinical data relating to case samples were collected from the JIA Registry maintained within the CHOP Division of Rheumatology for the CHOP cohort; clinical data relating to case samples from TSRHC, CMHC, MCRI, and OUH were drawn from records provided by the respective sites and stored in a de-identified database at the Center for Applied Genomics of the CHOP Research Institute.

[a]Revised ILAR criteria.[1] For this study, a patient was considered to be rheumatoid factor (RF)-negative based on a single test; patients for whom the RF was indeterminant (27 patients) were excluded from subtype analysis.

[b]JIA Data Set: TSRHC; Texas Scottish Rite Hospital for Children, Dallas, Tex., USA; CMHC; Children's Mercy Hospitals and Clinics, Kansas City, Mo., USA; CHOP; The Children's Hospital of Philadelphia, Philadelphia, Pa., USA; MCRI; Murdoch Childrens Research Institute, Melbourne, Australia; OUH; Department of Rheumatology, Oslo University Hospital, Rikshospitalet, Oslo, Norway.

[c]CCHMC, Cincinnati Children's Hospital Medical Center; controls for this dataset were comprised of 649 local and 2400 out-of-study controls (see Methods); proxy SNPs of the two JIA subtypes from CCHMC were not included in the meta-analysis (Table 2).

The control subjects used included 6500 unrelated and disease-free children recruited from within the CHOP Healthcare Network. Control subjects (average age 7.9±6.0 SD years; 53.74% males, 46.26% females) had no history of JIA or other chronic illnesses and were screened as negative for a diagnosis of autoimmune diseases, based on data from CHOP's electronic health record and by intake questionnaires obtained by the recruiting staff from the Center for Applied Genomics. All pediatric controls passed stringent quality control (QC), as detailed below; post-QC, controls were selected by matching algorithms on the basis of multidimensional scaling (MDS) analysis.[18,19] In brief, although all subjects were of self-reported European American ancestry, we combined >10,000 control subjects with cases and performed MDS to infer a homogeneous group of subjects of European ancestry. Cases from the third replication cohort (OUH) were subsequently analyzed, using the 3000 well-characterized subjects from the Wellcome Trust Case-Control Consortium (WTCCC[19]) as controls.

Six cases from the CHOP cohort and eleven cases from the OUH cohort were excluded due to a low call rate. In addition, 202 cases were excluded due to MDS correction: 76 cases were removed from the discovery cohort; 8 cases were removed from the first replication cohort (CHOP); 67 cases were removed from the second replication cohort (MCRI); and 51 cases were removed from the third replication cohort (OUH), yielding 1166 ethnically-matched JIA cases and 9500 controls (Table 4).

TABLE 4

The most significantly associated SNPs in the vicinity of CXCR4 on chromosome 2q21.

| | | | | Discovery (TSRHC + CMHC) | | | | |
|---|---|---|---|---|---|---|---|---|
| | | Position [a] (NCBI | Minor/ Major | Minor allele frequency | | | | |
| CHR | SNP | 36) | Alleles[a] | Case | Control | p value | OR[b] | 95% CI |
| 2 | rs953387 | 136623640 | G/T | 0.29 | 0.41 | 2.07E−10 | 0.59 | 0.50-0.69 |
| 2 | rs1123848 | 136661499 | T/C | 0.28 | 0.39 | 3.89E−10 | 0.59 | 0.50-0.70 |
| 2 | rs4954564 | 136611978 | G/A | 0.30 | 0.41 | 3.08E−09 | 0.61 | 0.52-0.72 |
| 2 | rs10221893 | 136730076 | C/T | 0.39 | 0.51 | 4.58E−09 | 0.63 | 0.54-0.74 |
| 2 | rs6430612 | 136722668 | C/T | 0.39 | 0.51 | 7.98E−09 | 0.64 | 0.55-0.74 |
| 2 | rs1016269 | 136657132 | A/G | 0.15 | 0.24 | 4.01E−08 | 0.56 | 0.46-0.69 |
| Sample size | | | | 388 | | | | |
| Number of cases | | | | | | | | |
| Number of controls | | | | 2500 | | | | |
| Total sample number | | | | 2888 | | | | |

TABLE 4-continued

The most significantly associated SNPs in the vicinity of CXCR4 on chromosome 2q21.

| | | Replication 1 (CHOP) | | | Replication 2 (MCRI) | | | Replication 3 (OUH) | | | p value |
|---|---|---|---|---|---|---|---|---|---|---|---|
| | | Minor allele frequency | | | Minor allele frequency | | | Minor allele frequency | | | (Combined Meta- |
| CHR | | Case | Control | p value | Case | Control | p value | Case | Control | p value | analysis) |
| 2 | | 0.35 | 0.41 | 0.01 | 0.35 | 0.42 | 0.02 | 0.21 | 0.26 | 5.52E−04 | 1.03E−13 |
| 2 | | 0.35 | 0.40 | 0.04 | 0.33 | 0.40 | 0.01 | NA | NA | NA | 6.11E−11 |
| 2 | | 0.35 | 0.42 | 0.01 | 0.35 | 0.42 | 0.02 | 0.21 | 0.26 | 7.16E−04 | 3.80E−13 |
| 2 | | 0.50 | 0.53 | 0.31 | 0.46 | 0.52 | 0.05 | 0.31 | 0.33 | 3.23E−01 | 7.32E−07 |
| 2 | | 0.49 | 0.53 | 0.17 | 0.46 | 0.52 | 0.05 | 0.31 | 0.33 | 3.23E−01 | 3.84E−07 |
| 2 | | 0.19 | 0.25 | 0.02 | 0.21 | 0.25 | 0.11 | 0.12 | 0.16 | 4.91E−03 | 4.85E−10 |
| Sample size Number of cases | | 182 | | | 154 | | | 442 | | | 1166 |
| Number of controls | | 2000 | | | 2000 | | | 3000 | | | 9500 |
| Total sample number | | 2182 | | | 2154 | | | 3442 | | | 10,666 | p value, basic allelic test p value;
OR, odds ratio;
CI, confidence interval;
p value (combined), meta-analysis p value in all 4 cohorts.
[a]The chromosome coordinates and allele designations are on the basis of the forward strand of the NCBI 36 genome assembly.
[b]The odds ratio is calculated with respect to the minor allele.

TABLE 5

Association of rs953387 with the JIA subtypes.

| JIA Subtypes[a] | CHR | SNP | Position[b] (NCBI 36) | Sample Number | | Minor/ Major Alleles | Minor Allele Frequency | | Combined Meta-analysis | | |
|---|---|---|---|---|---|---|---|---|---|---|---|
| | | | | Case | Control | | Case | Control | p value | OR[c] | 95% CI |
| Oligoarthritis, persistent + extended | 2 | rs953387 | 136623640 | 437 | 5000 | G/T | 0.28 | 0.32 | 3.42E−04 | 0.84 | 0.72-0.98 |
| Polyarthritis, RF negativ[#] | 2 | rs953387 | 136623640 | 249 | 4000 | G/T | 0.27 | 0.30 | 4.09E−03 | 0.88 | 0.72-1.08 |
| Oligoarthritis + Polyarthritis, RF negative[d] | 2 | rs953387 | 136623640 | 1500 | 9049 | G/T | 0.31 | 0.33 | 6.31E−05 | 0.90 | 0.83-0.98 |
| Polyarthritis, RF positive | 2 | rs953387 | 136623640 | 54 | 3500 | G/T | 0.25 | 0.28 | 1.25E−02 | 0.85 | 0.55-1.31 |
| Systemic arthritis | 2 | rs953387 | 136623640 | 103 | 4000 | G/T | 0.26 | 0.30 | 4.04E−03 | 0.82 | 0.6-1.12 |
| Enthesitis-related arthritis | 2 | rs953387 | 136623640 | 138 | 4000 | G/T | 0.24 | 0.30 | 3.82E−04 | 0.73 | 0.55-0.96 |
| Psoriatic arthritis | 2 | rs953387 | 136623640 | 87 | 3500 | G/T | 0.32 | 0.28 | 0.580 | 1.18 | 0.85-1.63 |
| Undifferentiated arthritis | 2 | rs953387 | 136623640 | 71 | 3500 | G/T | 0.29 | 0.28 | 0.175 | 1.02 | 0.71-1.47 | p value, basic allelic test p value;
OR, odds ratio; CI, confidence interval;
p value (combined), meta-analysis p value in all cohorts.
[a]Subtype sample number for each cohort is shown in Supplemental Table 1. For Oligoarthritis + Polyarthritis, RF negative, we received a fifth cohort of 814 cases and 3049 controls from Cincinnati Children's Hospital Medical Center (CCHMC) genotyped on Affymetrix, and are presenting the imputed data.
[b]The chromosome coordinates and allele designations are on the basis of the forward strand of the NCBI 36 genome assembly.
[c]The odds ratio is calculated with respect to the minor allele.
[d]RF status unknown for 27 samples from CMHC. These were included in the analysis of the JIA discovery cohort, but not in the subtype analysis.

A secondary association analysis of the various JIA subtypes also was performed in 1139 of our 1166 JIA cases in comparison with controls (Table 5). Excluded from our subtype analysis were 27 of the CMHC cases; these participants fulfilled clinical criteria for the polyarthritis subtype of JIA, but rheumatoid factor status was unknown (Table 2). In this analysis, we additionally included imputed data from a cohort of 814 subjects with either oligoarthritis or polyarthritis, RF negative, in comparison with 3039 controls (639 of whom were local and 2400 out-of-study controls[20]) from the Cincinnati Children's Hospital Medical Center (CCHMC; Cincinnati, Ohio). Subjects from this site were genotyped on the Affymetrix 6.0 platform and have been described previously.[9]

The study was approved by the institutional review boards of TSRHC, CMHC, CHOP, MCRI, OUH, and CCHMC, and was compliant with HIPAA regulations. Parental written informed consent was obtained from all participants in this study for the purpose of DNA collection and genotyping.

Procedures and Study Design

We performed GWAS in our discovery cohort (TSRHC+ CMHC), including only those individuals of inferred European ancestry, followed by replication analysis of positive signals in three independent cohorts, including patients from CHOP (cohort 1), MCRI (cohort 2) and OUH (cohort 3) in keeping with GWAS standards.[21,22] Population structure (genetic differences within an apparently homogeneous population) was investigated using MDS. A total of 1166 cases and 9500 controls were inferred as having European ancestry using these procedures. Our genetic association data are reported according to Strengthening the Reporting of Genetic Association studies (STREGA) guidelines.[23]

Genotyping

All JIA cases were recruited in the U.S., Australia, or Norway. JIA cases and U.S. controls in our discovery cohort were genotyped using the Human610-Quad arrays (with 610,000 SNP markers). The overall genotype call rate was 99.95% after QC in the discovery cohort. JIA cases in the replication cohorts and their matching controls were genotyped using either the Illumina HumanHap550 BeadChip (with 550,000 single nucleotide polymorphism [SNP] markers) or the Human610-Quad arrays (with 610,000 SNP markers). While about 98% of SNPs are identical on these two platforms, their performance differs; we, therefore, examined only SNPs that demonstrated significance in the 610,000 discovery dataset in this study. JIA cases and local controls from CCHMC were genotyped using the Affymetrix Genome-Wide Human SNP Array 6.0, as described previously.[9] The publicly available control data set from the Wellcome Trust Case Control Consortium [WTCCC-1][19] and Molecular Genetics of Schizophrenia, non-Gain[20] were genotyped using the Affymetrix GeneChip 500K Mapping Array Set or the Affymetrix 6.0 GWAS Array, respectively.

The criteria for SNP selection for the discovery and replication stages have been previously reported by our laboratory[24] and are described below. We used Markov Chain Haplotyping (MACH; URLs) for genotype imputation on markers that were not present in the genotyping platforms for our JIA cohort.[25] The default two-step procedure was adopted for imputation. Whole-genome genotype imputation was performed on the autosomal markers on the basis of phased haplotypes (release 22) for the HapMap CEU population (URLs). We removed all markers with MACH $r^2$ measure of <0.3, and zeroed out imputed genotypes with a posterior probability of <0.9.

Quality Control

We applied QC filters to exclude unreliable samples prior to association analysis. A sample was excluded if the genotype call rate was <95% or if the sample showed excess or deficient heterozygosity (inbreeding coefficient $|F|>0.1$). Cryptic relatedness or erroneous duplicates were evaluated using pair-wise identity-by-descent estimation, and the sample with lower genotype call rate was removed from each identified relative pair. For this analysis, we eliminated SNPs with genotype call rate <98%, with minor allele frequency (MAF)<1% in either cases or controls, or if there was significant departure from Hardy-Weinberg equilibrium (p<0.0001). In the discovery cohort, there were 56,873 SNPs with missing rate >2%. A total of 518,907 SNPs passed QC and were included in analysis. In addition, we used these genotyped SNPs and 120 phased chromosomes from the HapMap CEU samples (HapMap release 22, NCBI build 36) to impute genotypes for untyped SNPs using MACH 1.0 software.[25] Imputed SNPs with MAF <0.01 in either cases or controls and SNPs with poor imputation quality ($r^2<0.3$) were excluded.

Population Stratification

Patients with JIA in the discovery and replication cohorts were genetically matched with unrelated controls of European ancestry using the MDS algorithm employed in PLINK[18] for inferring population structure (URLs). To help with our interpretation of the population genetics, we included 924 individuals from thirteen HapMap populations as positive controls in the MDS analysis. Comparing self-identified ancestry with the MDS-inferred ancestry confirmed the reliability of MDS to identify genetically inferred individuals of European ancestry. Thus, the probability of false-positive associations caused by potential problems such as population stratification between cases and control subjects was minimized. To confirm this, we created a Quantile-Quantile plot (QQ-plot) of p values obtained by the allelic test and calculated the inflation factor of test-statistics, λGC, using WGAViewer (URLs). The genomic inflation lambda in the three cohorts typed genome-wide (discovery and replication cohorts 1 and 2) were 1.11, 1.00, and 1.03, respectively. When we correct the chi-square statistics with the lambda in the discovery cohort using the stringent genomic control method, five SNPs still remain GW significant (p<$5\times10^{-8}$) in the discovery cohort and the replication cohorts are unaffected. These data suggest that the identified association of rs953387 in the GWAS is not a false positive but has a robust, true association with JIA.

Power Calculations

The statistical rationale for our sample size was as follows: We evaluated the power to detect association of tagSNPs with JIA using the software, Quanto (URLs) for a combined cohort of 1166 subjects and 9500 controls (at a significance level of $5\times10^{-8}$). To correct for multiple testing and achieve a family-wise error rate of 0.05, we fixed the significance level of the test at $5\times10^{-8}$ based on published criteria.[22] The size of the genetic relative risk, defined as the risk of having JIA in the presence of a genetic risk variant was varied from 1.1 to 2.5. We used a range of MAF at the SNPs of 0.05 to 0.45, and a log additive genetic model for the relative risk. As expected, the power increased with increasing levels of genotype relative risk (GRR) and marker allele frequencies. For example, even for a rare SNP with MAF of 0.05, we would have >80% power to detect association if GRR is >1.9. However, for a more common SNP with MAF of 0.25 or more, we would have >80% to detect association if GRR is >1.4. These calculations reflect our power to detect a single variant; if there are multiple variants influencing the trait (as we expect), the power to detect at least one of them is much better.[26] We were thus confident that given the available sample size we would have sufficient power to detect genetic variants with a wide range of effects on risk of developing JIA.

Gene Expression

WGAViewer (URLs) was used to test association between SNP genotypes and gene expression variation (eQTL), quantified in immortalized B-lymphocytes and T-cells, using the databases from the Sanger Institute Genevar project[27] (URLs) and the HapMap and GenCord projects.[28,29] As described by Stranger et al.,[27,30,31] transcript levels were measured using Illumina's human whole-genome expression (WG-6 version 1) arrays,[32] which contained 47,294 probes, with two or more unique oligonucleotide probes per gene, in four technical replicates. Raw intensity values were normalized on a log scale using a quantile normalization method[33] across the four replicates for each individual, to obtain a single expression level per individual.[27,30,31] There was a high degree of correlation in the transcript level measurements generated on this genome-wide array within and between arrays ($r^2=0.96$-$0.99$) and with expression measurements generated on Illumina's low-density (~700 genes) custom arrays.[31]

Statistical Analyses

For genotyped SNPs, association was tested by basic allelic test (chi-square test) and the odds ratio was calculated with respect to the minor allele using PLINK[1]. The estimated genomic control inflation factor lambda (λ)[34] an indicator of potential population stratification, was calculated using WGAViewer (URLs). For imputed SNPs, association was examined using MACH 1.0 software[25] for untyped SNPs that were in strong linkage disequilibrium (LD) with markers present in the genotyping platforms ($r^2>0.9$) for our JIA cohort. The default two-step procedure was adopted for imputation. For comparison of our association results for JIA with the WTCCC rheumatoid arthritis (RA) cohorts,[19] we also used MACH to infer the genotype on untyped markers.

The criteria for SNP selection at each stage were based on the approach of Kugathasan and colleagues.[24] In stage 1 of this study (discovery analysis), 518,907 genotyped SNPs were studied. A significant finding was defined a priori by published criteria[22] as $p<5\times10^{-8}$. Criteria for selection of SNPs for stage 2 (replication analysis) were a GW-significant p value as well as multiple hits at the same locus, to avoid spurious association. Replication was claimed when the direction of effect was the same and the p value was lower than the locus-specific threshold (0.05), after correction for multiple tests.

Near identical results were obtained in permutation tests—often referred to as the gold standard for randomization[35]—performed for the six genome-wide significant SNPs in the discovery cohort. The corrected p value based on 10,000 permutations for the most significant SNP rs4954564 (nominal p=0.009) in replication 1 is 0.0274 (corrected by the P_ACT program as $0.027^{35}$), suggesting the effective number of independent tests is about three instead of six. This SNP has a p value of 0.017 in replication 2 (no further correction is needed as we tested only this one in replication cohort 2). The corrected p value for the whole SNP set based on 10,000 permutations, testing the null hypothesis that no SNP from this set is associated with JIA, is 0.0274 and 0.0232 for replications 1 and 2, respectively (0.027 and 0.021 by the P_ACT program). For such a SNP set analysis, PLINK provides a similar permutation test but considering mean instead of minimum. The p values reported by PLINK based on 10,000 permutations are 0.04 and 0.03 for replications 1 and 2, respectively. Thus, no matter whether based on individual SNPs or SNP sets, permutation-based tests, P_ACT, or PLINK, all tests successfully confirm the association at the 0.05 level.

Meta-analysis is a powerful method for testing the significance of a replication study, combining the results of several studies that address a set of related research hypotheses. For our meta-analysis, we used a weighted Z-score method with METAL[36] (URLs), which accounts for the direction of association relative to a consistent reference allele. In this method, p values are combined across studies; the weight for each cohort is calculated by taking into account sample size and direction of effect. All meta-analyses comply with MOOSE guidelines (URLs).

To test association between SNP genotypes and gene expression, we used publicly available data from genome-wide expression analysis of quantitative trait loci (eQTL) of the 270 individuals genotyped in the HapMap Project (including 30 Caucasian trios of Northern and Western European origin KEUI[27,28,30,31]) and the 85 individuals of the GenCord project (a collection of cell lines from umbilical cords of individuals of Western European origin[29]). To associate SNP genotypes with gene expression, a p-value was calculated by a linear regression model.[30] Specifically, the additive effect of a SNP allele was tested by coding the genotypes of the SNP as 0, 1, and 2 (corresponding to the counts of the minor allele in each genotype) and performing a linear regression of this variable with the gene expression values.

The following examples are provided to illustrate certain embodiments of the invention. They are not intended to limit the invention in any way.

Example I

Figure 1:
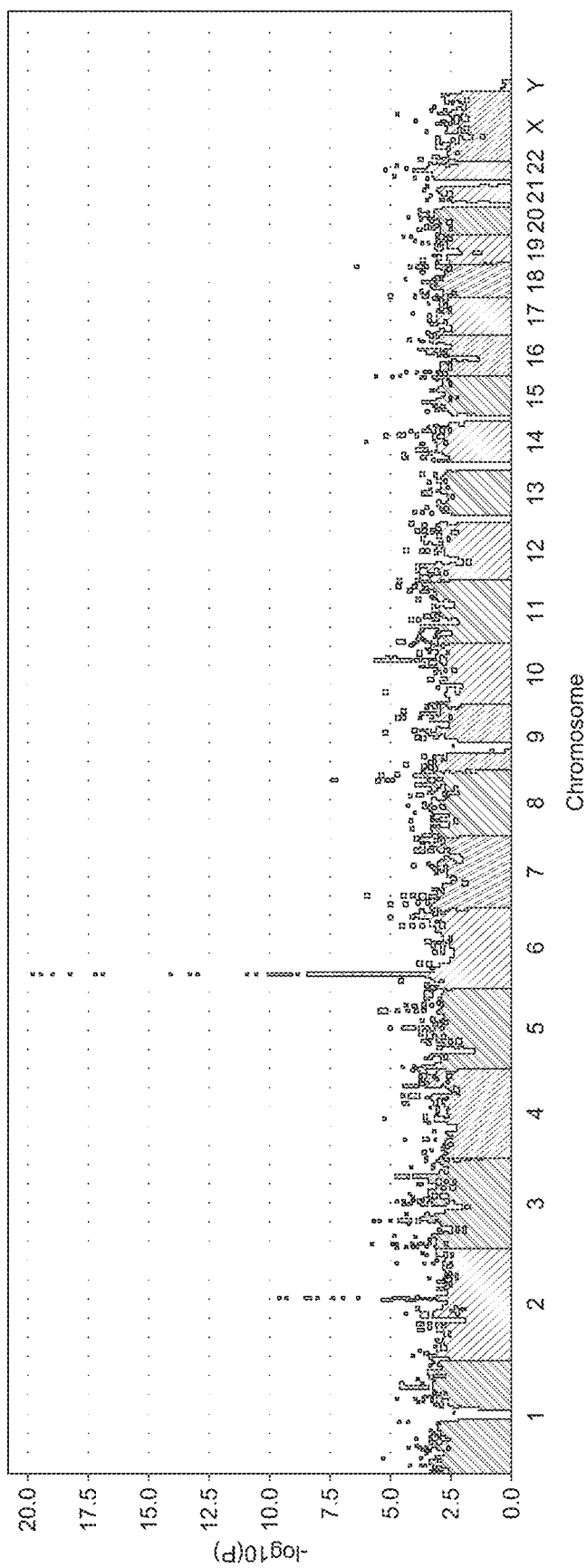
FIG. 1. Genome-wide association results for the 2q21 region. Manhattan plot showing the $-\log_{10}(p$ values) of SNPs from the GWAS of the discovery cohort. p values down to $10^{-20}$ only are shown for optimal resolution; p values for the MHC on chromosome 6 reached $2.63 \times 10^{-25}$.
Figure 2:
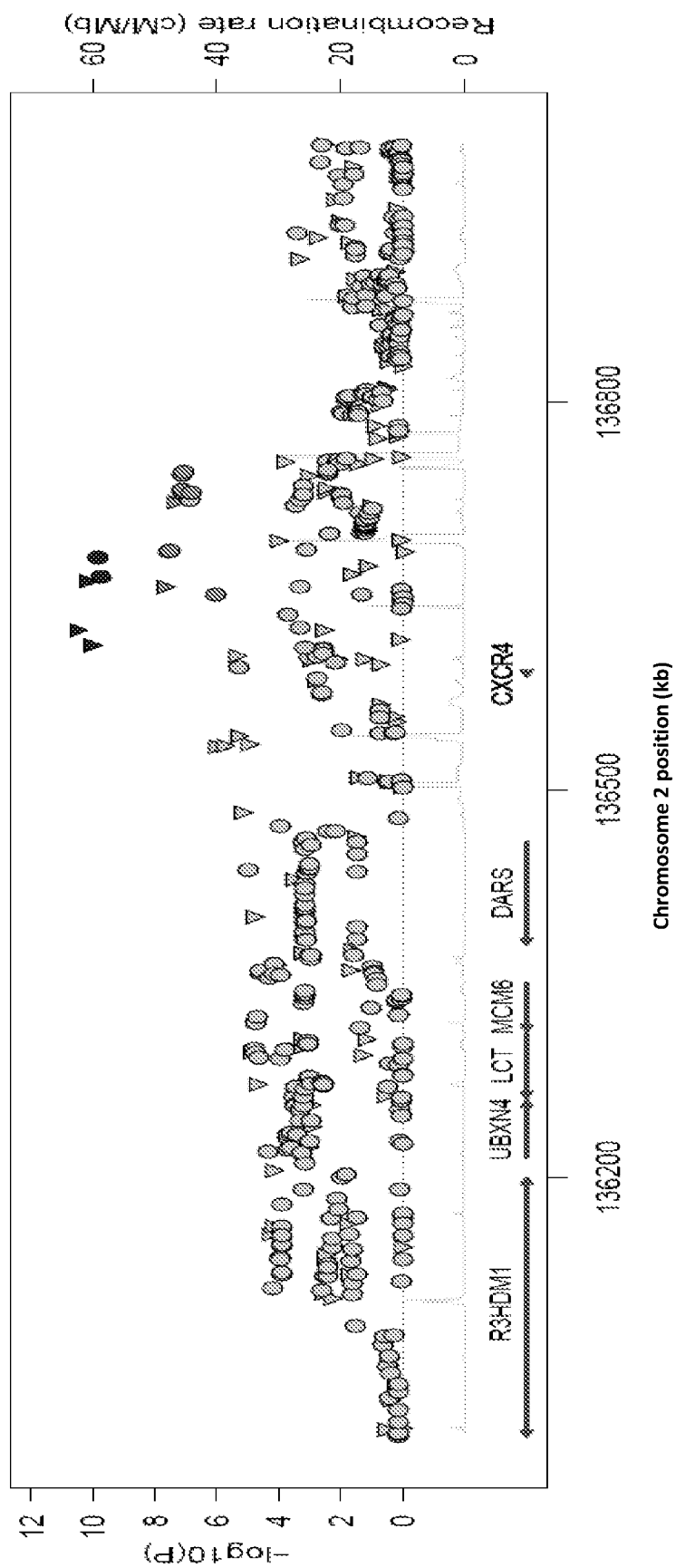
FIG. 2. Association results for genotyped and imputed SNPs in the 2q21 region. Genotyped (triangle) and imputed (circles) SNPs are plotted with their combined p values in the three cohorts typed genome-wide (discovery and replication cohorts 1 and 2). SNPs are colored on the basis of their correlation with rs953387 (red: $r^2 \geq 0.8$; orange: $0.5 \leq r^2 < 0.8$; yellow: $0.2 \leq r^2 < 0.5$). Estimated recombination rates from HapMap data are plotted to reflect the local linkage disequilibrium (LD) structure.
Figure 3:
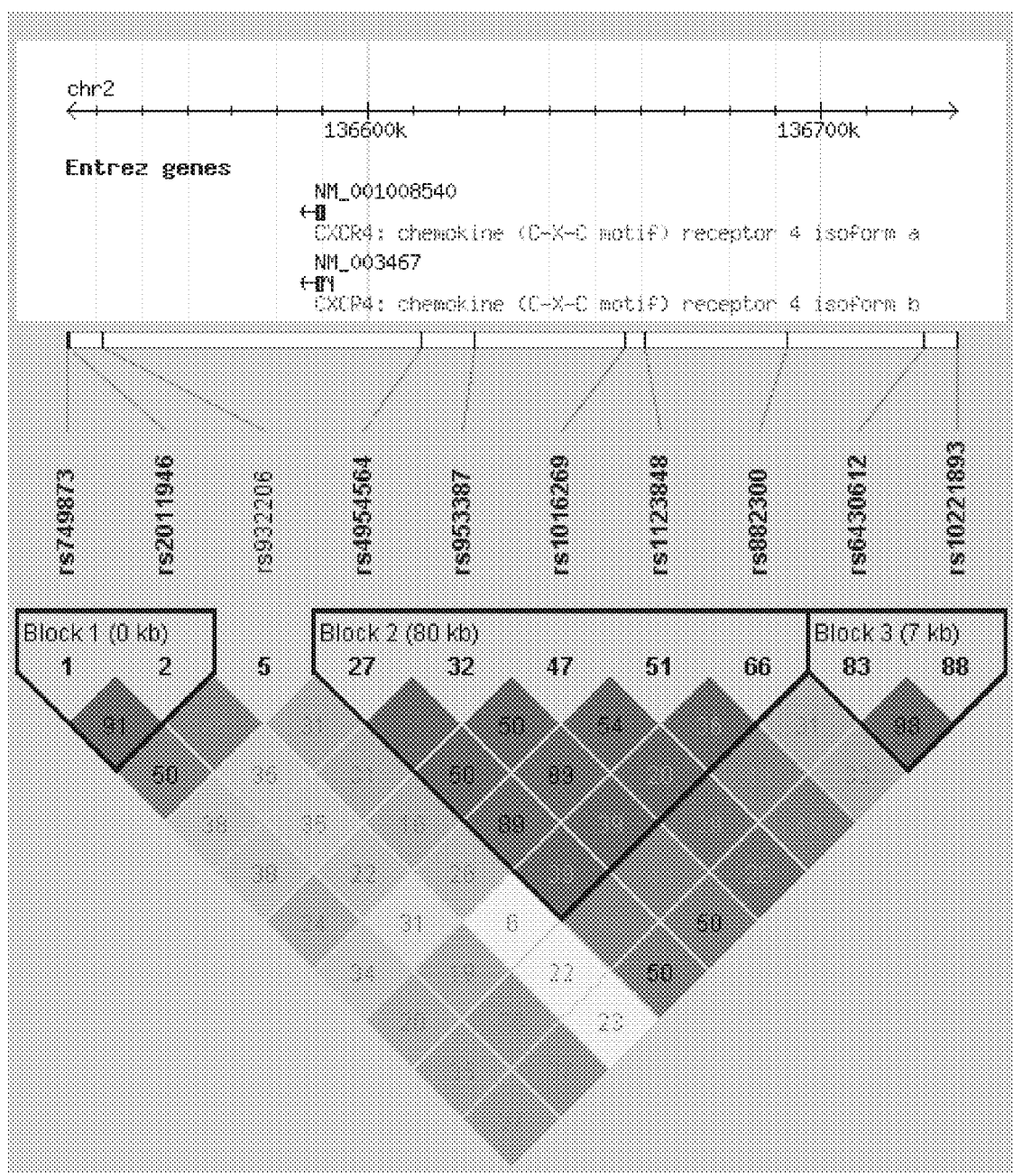
FIG. 3. Representation of the chromosome 2q21 associated interval.

The discovery analysis included 388 children with JIA and 2500 genetically matched unrelated controls of European ancestry with high-quality SNP array data (Table 4 and Tables 1-3). We observed genome-wide significant associations ($p<5\times10^{-8}$) with JIA at two loci in the discovery cohort (FIG. 1). In addition to a strong association with the MHC on 6p21 (Table 6), six intergenic SNPs located on 2q21 reached genome-wide significance (Table 4 and Table 7), with the most significant marker being rs953387 ($p=2.07\times10^{-10}$; OR 0.59, 95% CI 0.50-0.69). Five of these SNPs still remained GW significant ($p<5\times10^{-8}$) after correction for the estimated genomic inflation lambda ($\lambda$; an indicator of potential population stratification) using the stringent genomic control method (see Subjects and Methods, Population stratification). The protective OR of 0.59 for the minor allele of rs953387 corresponds to an OR of 1.70 for the major allele (which, in this case, confers risk). Four additional SNPs at the same locus had p values below $1\times10^{-4}$ (Table 8). These 10 SNPs map to three linkage disequilibrium blocks on 2q21 spanning the CXCR4 gene region (FIGS. 2 and 3).

TABLE 6

Genome-wide association results ($p < 5 \times 10^{-8}$) in the discover cohort) for the MHC

| CHR | SNP | BP[b] | Gene | Minor/Major Alleles[b] | Case_MAF | Control_MAF | p value (Discovery) | OR[c] | p value (Combined Meta-analysis) |
|---|---|---|---|---|---|---|---|---|---|
| 6 | rs2395148 | 32429532 | C6orf10 | T/G | 0.095 | 0.025 | 2.63E−23 | 4.08 | 7.95E−38 |
| 6 | rs2073048 | 32443411 | C6orf10 | T/C | 0.242 | 0.119 | 1.31E−20 | 2.36 | 3.43E−26 |
| 6 | rs7770048 | 32442732 | C6orf10 | T/C | 0.242 | 0.119 | 1.51E−20 | 2.36 | 1.86E−26 |
| 6 | rs4248166 | 32474399 | BTNL2 | C/T | 0.296 | 0.160 | 3.03E−20 | 2.21 | 3.19E−26 |
| 6 | rs2294884 | 32475237 | BTNL2 | C/A | 0.299 | 0.164 | 8.38E−20 | 2.18 | 4.19E−25 |
| 6 | rs13192471 | 32779081 | near HLA-DQB1 | C/T | 0.244 | 0.136 | 6.32E−15 | 2.05 | 3.70E−23 |
| 6 | rs6907322 | 32432923 | C6orf10 | A/G | 0.295 | 0.177 | 7.60E−15 | 1.95 | 1.78E−18 |
| 6 | rs1794275 | 32779226 | near HLA-DQB1 | T/C | 0.275 | 0.163 | 4.99E−14 | 1.94 | 4.80E−16 |
| 6 | rs9268365 | 32441417 | C6orf10 | T/G | 0.296 | 0.181 | 5.06E−14 | 1.91 | 4.41E−18 |
| 6 | rs10947262 | 32481290 | BTNL2 | T/C | 0.174 | 0.088 | 9.91E−14 | 2.18 | 1.84E−18 |
| 6 | rs7765379 | 32788906 | near HLA-DQA2 | G/T | 0.188 | 0.098 | 9.91E−14 | 2.13 | 8.27E−16 |

TABLE 6-continued

Genome-wide association results ($p < 5 \times 10^{-8}$) in the discover cohort) for the MHC

| CHR | SNP | BP[b] | Gene | Minor/Major Alleles[b] | Case_MAF | Control_MAF | p value (Discovery) | OR[c] | p value (Combined Meta-analysis) |
|---|---|---|---|---|---|---|---|---|---|
| 6 | rs3763313 | 32484449 | near BTNL2 | C/A | 0.284 | 0.180 | 1.29E−11 | 1.80 | 1.60E−14 |
| 6 | rs2071286 | 32287874 | NOTCH4 | A/G | 0.331 | 0.222 | 2.30E−11 | 1.74 | 2.17E−14 |
| 6 | rs1265048 | 31189388 | near C6orf15 | G/A | 0.457 | 0.338 | 9.57E−11 | 1.65 | 1.62E−10 |
| 6 | rs1035798 | 32259200 | AGER | T/C | 0.370 | 0.261 | 2.31E−10 | 1.67 | 1.76E−16 |
| 6 | rs2395185 | 32541145 | near HLA-DRA | T/G | 0.197 | 0.306 | 5.74E−10 | 0.56 | 3.27E−18 |
| 6 | rs411326 | 32319295 | near NOTCH4 | A/G | 0.342 | 0.244 | 7.39E−09 | 1.61 | 2.97E−06 |
| 6 | rs2516049 | 32678378 | near HLA-DRB1 | G/A | 0.196 | 0.295 | 1.05E−08 | 0.58 | 1.20E−19 |
| 6 | rs477515 | 32677669 | near HLA-DRB1 | T/C | 0.196 | 0.295 | 1.20E−08 | 0.58 | 1.46E−19 |
| 6 | rs2301226 | 33142574 | HLA-DPA1 | T/C | 0.214 | 0.137 | 1.52E−08 | 1.72 | 1.40E−11 |
| 6 | rs17576984 | 32320963 | near NOTCH4 | T/C | 0.148 | 0.085 | 1.84E−08 | 1.87 | 1.72E−13 |
| 6 | rs570963 | 32397572 | C6orf10 | C/T | 0.175 | 0.107 | 3.09E−08 | 1.78 | 5.09E−11 |
| 6 | rs3868075 | 31275794 | HCG27 | C/T | 0.501 | 0.397 | 4.40E−08 | 1.52 | 2.23E−04 |
| 6 | rs4713447 | 31270942 | near HCG27 | G/A | 0.501 | 0.397 | 4.45E−08 | 1.52 | 2.28E−04 |

BP, base pair chromosome coordinates;
MAF, minor allele frequencies in discovery cohort;
p value, basic allelic test p value;
OR, odds ratio in discovery cohort;
p value (combined), meta-analysis p value in the three cohorts typed genome-wide (discovery and replication cohorts 1 and 2).
[b]The chromosome coordinates and allele designations are on the basis of the forward strand of the NCBI 36 genome assembly.
[c]The odds ratio is calculated with respect to the minor allele.

TABLE 7

Genotype counts for the six SNPs in the vicinity of CXCR4 on chromosome 2q21

| SNP | Minor/Major Alleles | Discovery (TSRHC + CMHC) Genotypes in cases[a] | Discovery (TSRHC + CMHC) Genotypes in controls | Replication 1 (CHOP) Genotypes in cases | Replication 1 (CHOP) Genotypes in controls | Replication 2 (MCRI) Genotypes in cases | Replication 2 (MCRI) Genotypes in controls | Replication 3 (OUH) Genotypes in cases | Replication 3 (OUH) Genotypes in controls |
|---|---|---|---|---|---|---|---|---|---|
| rs953387 | G/T | 35/154/199 | 422/1198/880 | 22/82/77 | 373/910/716 | 21/65/68 | 377/909/713 | 17/148/277 | 232/1086/1619 |
| rs1123848 | T/C | 32/150/206 | 396/1172/932 | 21/84/77 | 350/902/747 | 18/64/72 | 360/889/751 | 19/146/277 | NA |
| rs4954564 | G/A | 37/158/193 | 429/1196/875 | 22/83/77 | 375/916/695 | 21/66/67 | 381/911/699 | 18/147/277 | 231/1083/1623 |
| rs10221893 | C/T | 66/174/148 | 625/1287/588 | 37/68/38 | 473/944/583 | 38/67/49 | 493/926/581 | 34/209/199 | 392/1167/1373 |
| rs6430612 | C/T | 66/174/148 | 620/1288/592 | 45/88/49 | 471/949/577 | 37/68/49 | 498/925/577 | 34/209/199 | 392/1165/1376 |
| rs1016269 | A/G | 13/91/284 | 149/900/1451 | 7/56/119 | 122/741/1137 | 6/51/97 | 132/718/1149 | 7/95/340 | 104/756/2077 |

[a]The genotype counts are listed as homozygous genotypes of minor allele/heterozygous genotypes/homozygous genotypes of major allele.

TABLE 8

Genome-wide association results for CXCR4 (p < 1 × 10$^{-3}$ in the discovery cohort) in our JIA cohort and in the WTCCC RA cohort

| SNP | BP[a] | Minor/Major Alleles[a] | Case_MAF | Control_MAF | p value (Discovery) | p value (Combined Meta-analysis) | Trend p value in WTCCC cohort |
|---|---|---|---|---|---|---|---|
| rs953387 | 136623640 | G/T | 0.289 | 0.408 | 2.07E−10 | 2.87E−11 | 0.240 |
| rs1123848 | 136661499 | T/C | 0.276 | 0.393 | 3.89E−10 | 6.11E−11 | NA |
| rs4954564 | 136611978 | G/A | 0.299 | 0.411 | 3.08E−09 | 8.58E−11 | 0.239 |
| rs10221893 | 136730076 | C/T | 0.394 | 0.507 | 4.58E−09 | 9.31E−08 | 0.191 |
| rs6430612 | 136722668 | C/T | 0.394 | 0.506 | 7.98E−09 | 4.08E−08 | 0.192 |
| rs1016269 | 136657132 | A/G | 0.151 | 0.240 | 4.01E−08 | 1.90E−08 | 0.174 |
| rs749873 | 136533558 | C/T | 0.340 | 0.436 | 4.22E−07 | 8.94E−07 | 0.786 |
| rs2011946 | 136534086 | G/T | 0.325 | 0.408 | 1.03E−05 | 1.59E−06 | 0.846 |
| rs932206 | 136541742 | G/A | 0.427 | 0.509 | 1.83E−05 | 4.53E−06 | 0.801 |
| rs882300 | 136692725 | A/G | 0.454 | 0.377 | 4.37E−05 | 8.51E−05 | 0.929 |
| rs12466743 | 136937875 | G/A | 0.057 | 0.100 | 1.37E−04 | 1.37E−04 | 0.047 |
| rs16834223 | 136910906 | G/A | 0.058 | 0.101 | 1.38E−04 | 3.94E−04 | 0.045 |
| rs4954599 | 136753856 | G/A | 0.246 | 0.313 | 1.58E−04 | 1.41E−04 | 0.548 |
| rs2090660 | 136535189 | A/G | 0.229 | 0.294 | 2.17E−04 | 9.63E−06 | 0.692 |
| rs6756490 | 136723546 | A/G | 0.166 | 0.223 | 3.87E−04 | 4.44E−04 | 0.418 |
| rs4477975 | 136725476 | G/A | 0.166 | 0.222 | 4.49E−04 | 5.02E−04 | 0.419 |
| rs953388 | 136623599 | A/G | 0.104 | 0.152 | 5.14E−04 | 2.50E−03 | 0.144 |
| rs2056296 | 136603782 | T/C | 0.084 | 0.126 | 6.93E−04 | 3.87E−06 | 0.454 |
| rs4074120 | 136743057 | C/T | 0.228 | 0.286 | 8.16E−04 | 8.16E−04 | 0.361 |

BP, base pair chromosome coordinates;
MAF, minor allele frequencies in discovery cohort;
p value, basic allelic test p value;
p value (combined), meta-analysis p value in the three cohorts typed genome-wide (discovery and replication cohorts 1 and 2).
[a]The chromosome coordinates and allele designations are on the basis of the forward strand of the NCBI 36 genome assembly.

We next sought to replicate our 2q21 association signals in several independent cohorts of JIA patients. The first cohort included 182 JIA patients and an additional set of 2000 healthy controls recruited from the Children's Hospital of Philadelphia (CHOP; Philadelphia, Pa.; Replication 1; Table 1). Four SNPs showed evidence of association, and with the same direction of effect, as in the discovery cohort, with p values ranging from 0.01 to 0.04 (Table 4). To seek further evidence of replication, we examined a second independent cohort of 154 cases from the Murdoch Childrens Research Institute (MCRI; Melbourne, Australia; Replication 2; Table 1). A further additional set of 2000 genetically matched control samples from CHOP was utilized as a comparator for this analysis. Evidence of association with the same direction of effect was observed for five SNPs (p≤0.05) (Table 4). The SNPs at the CXCR4 locus survived correction in the two independent replication cohorts (p=0.0274 and 0.0232 for the set of SNPs in replication cohorts 1 and 2; see Subjects and Methods, Statistical analysis) and direction of effect is the same. A third independent cohort of 442 cases and 3000 controls from WTCCC replicates these data (OUH; Oslo, Norway; Replication 3; Table 1), with p values of 10$^{-4}$ to 10$^{-3}$ for three SNPs at this locus (Table 4).

Combined meta-analysis of all four cohorts indicated that four SNPs at the 2q21 locus were associated with JIA at a genome-wide significant level, with p values ranging from 1.03×10$^{-13}$ to 4.85×10$^{-10}$ (Table 4). In addition, three loci which previously have been implicated in JIA and several other autoimmune diseases[6,9,13]—the PTPN22 locus on 1p13, the IL2RA locus on 10p15, and the ANTXR2 locus on 4q21.21—were nominally associated with JIA: p=1.77× 10$^{-5}$, OR 1.65, 95% CI: 1.31-2.07 for rs2476601 near PTPN22 in our discovery cohort and in the subsequent meta-analysis (Tables 9 and FIG. 4); p=0.022, OR 0.84, 95% CI: 0.72-0.97 for rs706779 near IL2RA and p=0.0043, OR=0.72, 95% CI: 0.58-0.90 for rs17509015 near ANTXR2 in the discovery cohort (data not shown).

To determine if other variants that did not meet genome-wide significance criteria in the GWAS discovery cohort associate with JIA, we subsequently evaluated all SNPs with association p values <1×10$^{-5}$ for replication, following whole-genome imputation (see Subjects and Methods). Eight other non-MHC SNPs were genome-wide significant, although all but one had nearby SNPs in LD that did not support the association—and thus were discarded as likely genotyping errors—and none of these SNPs replicated when randomized for the number of tests performed (Table 10). Thus, the most significant non-MHC association signals—and the only ones that replicated—were those in the 2q21 region near CXCR4; rs953387 remained the most significantly associated SNP and another four imputed SNPs were identified with p values <5×10$^{-8}$, in support of the 2q21 locus (Table 11 and FIG. 2). Examination of the 2q21 region indicated that all genotyped and imputed SNPs with p values below 5×10$^{-8}$ reside within the same ~110 kilobase (kb) LD block (FIG. 5), suggesting that these SNPs are tagging the same variant(s). Taken together, several sources of converging evidence firmly establish that common genetic variants on 2q21 confer susceptibility to JIA.

TABLE 9

Genome-wide association results for PTPN22 (20 kb genomic regions on either side of the gene) in our JIA cohort and in the WTCCC RA cohort

| CHR | SNP | BP[a] | Gene | Minor/Major Alleles[a] | Case_MAF | Control_MAF | p value (Discovery) | OR[b] | p value (Combined Meta-analysis) | Trend p value in WTCCC cohort |
|---|---|---|---|---|---|---|---|---|---|---|
| 1 | rs3827733 | 114140112 | RSBN1 | G/A | 0.196 | 0.181 | 0.306 | 1.11 | 0.527 | 0.051 |
| 1 | rs3811021 | 114158186 | PTPN22 | C/T | 0.192 | 0.179 | 0.396 | 1.09 | 0.607 | 0.059 |
| 1 | rs2476599 | 114164982 | PTPN22 | A/G | 0.273 | 0.270 | 0.839 | 1.02 | 0.537 | 0.016 |
| 1 | rs3789607 | 114167957 | PTPN22 | C/T | 0.264 | 0.305 | 0.022 | 0.82 | 0.061 | 0.149 |
| 1 | rs2476601 | 114179091 | PTPN22 | A/G | 0.133 | 0.085 | 1.77E−5 | 1.65 | 6.18E−04 | 1.11E−16 |
| 1 | rs1217407 | 114195271 | PTPN22 | A/G | 0.271 | 0.245 | 0.127 | 1.14 | 0.385 | 2.30E−08 |
| 1 | rs1217418 | 114202754 | PTPN22 | A/G | 0.464 | 0.427 | 0.055 | 1.16 | 0.272 | 5.53E−04 |
| 1 | rs6665194 | 114219366 | between PTPN22 and BCL2L15 | A/G | 0.447 | 0.414 | 0.080 | 1.15 | 0.582 | 1.34E−04 |
| 1 | rs12566340 | 114221851 | BCL2L15 | T/C | 0.256 | 0.237 | 0.233 | 1.11 | 0.974 | 7.26E−09 |
| 1 | rs7529353 | 114221985 | BCL2L15 | A/G | 0.258 | 0.238 | 0.227 | 1.11 | 0.910 | 6.88E−09 |
| 1 | rs2358994 | 114230984 | BCL2L15 | A/G | 0.197 | 0.168 | 0.045 | 1.22 | 0.288 | 6.40E−12 |
| 1 | rs1217394 | 114235182 | near BCL2L15 | G/A | 0.305 | 0.333 | 0.123 | 0.88 | 0.304 | 0.217 |
| 1 | rs1217392 | 114235493 | between BCL2L15 and AP4B1 | T/G | 0.378 | 0.340 | 0.041 | 1.18 | 0.446 | 4.64E−05 |

BP, base pair chromosome coordinates;
MAF, minor allele frequencies in discovery cohort;
p value, basic allelic test p value;
OR, odds ratio in discovery cohort;
p value (combined), meta-analysis p value in the three cohorts typed genome-wide (discovery and replication cohorts 1 and 2).
[a]The chromosome coordinates and allele designations are on the basis of the forward strand of the NCBI 36 genome assembly.

TABLE 10

Results of the Discovery and combined analyses ($p < 1 \times 10^{-5}$), excluding the MHC and CXCR4

| CHR | SNP | BP[a] | Gene | Minor/Major Alleles[a] | Case_MAF | Control_MAF | p value (Discovery) | OR[b] | p value (Combined Meta-analysis) |
|---|---|---|---|---|---|---|---|---|---|
| 7 | rs7455060 | 118965081 | near KCND2 | G/A | 0.342 | 0.050 | 4.40E−152 | 9.85 | 2.55E−122 |
| 4 | rs4862110 | 183988023 | near ODZ3 | C/T | 0.497 | 0.176 | 1.83E−89 | 4.65 | 3.57E−84 |
| 20 | rs4814335 | 15001067 | MACROD2 | A/G | 0.493 | 0.175 | 6.77E−87 | 4.59 | 1.41E−55 |
| 5 | rs4957798 | 108472453 | FER | T/C | 0.392 | 0.186 | 1.01E−38 | 2.83 | 2.49E−27 |
| 5 | rs7726659 | 74513834 | near GCNT4 | G/A | 0.081 | 0.013 | 2.19E−33 | 6.90 | 2.24E−19 |
| 12 | rs7970177 | 13630255 | GRIN2B | T/C | 0.228 | 0.088 | 1.21E−30 | 3.05 | 6.57E−18 |
| 8 | rs2445610 | 128266270 | near MYC | G/A | 0.432 | 0.331 | 3.97E−08 | 1.54 | 0.049 |
| 8 | rs2456449 | 128262163 | near MYC | G/A | 0.416 | 0.317 | 4.85E−08 | 1.54 | 0.029 |
| 18 | rs6565965 | 73256562 | near GALR1 | C/T | 0.512 | 0.414 | 3.54E−07 | 1.48 | 1.67E−04 |
| 14 | rs2296322 | 64548701 | FNTB, MAX | C/A | 0.187 | 0.123 | 8.13E−07 | 1.65 | 3.70E−05 |
| 3 | rs11915523 | 108411619 | near CCDC54 | G/A | 0.056 | 0.024 | 1.19E−06 | 2.36 | 1.01E−03 |
| 16 | rs1129568 | 3423476 | near ZNF597 | C/T | 0.362 | 0.453 | 2.09E−06 | 0.69 | 4.67E−06 |
| 8 | rs2466031 | 128278791 | near MYC | G/A | 0.467 | 0.378 | 2.68E−06 | 1.44 | 0.140 |
| 5 | rs4958132 | 133019176 | near FSTL4 | C/T | 0.316 | 0.239 | 4.58E−06 | 1.47 | 0.066 |
| 9 | rs10867781 | 83423712 | TLE1 | T/C | 0.381 | 0.300 | 5.11E−06 | 1.44 | 6.71E−04 |
| 10 | rs2180563 | 33430188 | near NRP1 | A/G | 0.090 | 0.152 | 5.50E−06 | 0.55 | 0.254 |
| 5 | rs10491294 | 133018222 | near FSTL4 | C/T | 0.316 | 0.240 | 5.51E−06 | 1.46 | 0.060 |
| 14 | rs12891137 | 78693470 | NRXN3 | C/T | 0.142 | 0.090 | 5.81E−06 | 1.67 | 2.82E−03 |
| 8 | rs2456461 | 128251633 | near MYC | G/A | 0.468 | 0.383 | 6.76E−06 | 1.42 | 0.238 |
| 7 | rs11561808 | 16281469 | LOC729920 | C/T | 0.197 | 0.136 | 6.86E−06 | 1.56 | 9.27E−05 |

TABLE 10-continued

Results of the Discovery and combined analyses (p < 1 × 10$^{-5}$),
excluding the MHC and CXCR4

| CHR | SNP | BP[a] | Gene | Minor/ Major Alleles[a] | Case_ MAF | Control_ MAF | p value (Discovery) | OR[b] | p value (Combined Meta-analysis) |
|---|---|---|---|---|---|---|---|---|---|
| 6 | rs12524299 | 155769924 | NOX3 | T/C | 0.192 | 0.133 | 8.90E−06 | 1.56 | 8.33E−03 |
| 16 | rs7196196 | 3351856 | near OR2C1 | C/A | 0.407 | 0.493 | 9.46E−06 | 0.71 | 2.92E−04 |

BP, base pair chromosome coordinates;
MAF, minor allele frequencies in discovery cohort;
p value, basic allelic test p value;
OR, odds ratio in discovery cohort;
p value (combined), meta-analysis p value in the three cohorts typed genome-wide (discovery and replication cohorts 1 and 2).
[a]The chromosome coordinates and allele designations are on the basis of the forward strand of the NCBI 36 genome assembly.
[b]The odds ratio is calculated with respect to the minor allele.

TABLE 11

Genome wide association results for imputed SNPs (p < 1 × 10 − 4) in combined analysis in the vincinity of CXCR4 in our JIA cohort

| CHR | SNP | BP[a] | Type | Minor/ Major Alleles[a] | Case MAF | Control MAF | p value (Discovery) | OR[b] | p value (Combined Meta-analysis) |
|---|---|---|---|---|---|---|---|---|---|
| 2 | rs6716987 | 136679964 | Imputed | A/C | 0.273 | 0.390 | 4.86E−10 | 0.59 | 1.38E−10 |
| 2 | rs4954577 | 136665181 | Imputed | A | 0.274 | 0.390 | 5.99E−10 | 0.59 | 1.78E−10 |
| 2 | rs1519527 | 136684887 | Imputed | A/G | 0.150 | 0.239 | 3.90E−08 | 0.56 | 2.74E−08 |
| 2 | rs4954579 | 136684945 | Imputed | A/G | 0.150 | 0.239 | 4.04E−08 | 0.56 | 2.80E−08 |
| 2 | rs13024450 | 136731081 | Imputed | C/T | 0.394 | 0.504 | 1.17E−08 | 0.64 | 6.98E−08 |
| 2 | rs4452212 | 136732461 | Imputed | G/A | 0.394 | 0.504 | 1.17E−08 | 0.64 | 7.15E−08 |
| 2 | rs13004902 | 136744150 | Imputed | A/G | 0.394 | 0.504 | 1.17E−08 | 0.64 | 7.52E−08 |
| 2 | rs12691881 | 136746138 | Imputed | A/G | 0.394 | 0.504 | 1.24E−08 | 0.64 | 8.00E−08 |
| 2 | rs13018756 | 136724705 | Imputed | C/T | 0.394 | 0.502 | 2.41E−08 | 0.65 | 1.23E−07 |
| 2 | rs4072435 | 136730371 | Imputed | C/T | 0.394 | 0.502 | 2.13E−08 | 0.64 | 1.45E−07 |
| 2 | rs11674937 | 136650999 | Imputed | C/G | 0.174 | 0.264 | 1.38E−07 | 0.59 | 9.15E−07 |
| 2 | rs9973445 | 136595086 | Imputed | C/G | 0.084 | 0.126 | 8.61E−04 | 0.64 | 5.23E−06 |
| 2 | rs12615624 | 136438073 | Imputed | G/A | 0.262 | 0.331 | 1.48E−04 | 0.72 | 9.90E−06 |
| 2 | rs745500 | 136299662 | Imputed | G/A | 0.269 | 0.340 | 9.28E−05 | 0.71 | 1.62E−05 |
| 2 | rs7579771 | 136296730 | Imputed | A/T | 0.269 | 0.340 | 8.49E−05 | 0.71 | 1.66E−05 |
| 2 | rs3754686 | 136319746 | Imputed | T/C | 0.268 | 0.341 | 6.36E−05 | 0.71 | 1.83E−05 |
| 2 | rs3769005 | 136319836 | Imputed | C/G | 0.268 | 0.341 | 6.36E−05 | 0.71 | 1.83E−05 |
| 2 | rs4954490 | 136324701 | Imputed | G/A | 0.268 | 0.341 | 6.65E−05 | 0.71 | 1.87E−05 |
| 2 | rs892715 | 136293047 | Imputed | T/C | 0.269 | 0.340 | 8.74E−05 | 0.71 | 2.22E−05 |
| 2 | rs1435576 | 136358352 | Imputed | T/A | 0.274 | 0.352 | 2.73E−05 | 0.69 | 2.42E−05 |
| 2 | rs309125 | 136360025 | Imputed | T/C | 0.274 | 0.352 | 2.86E−05 | 0.69 | 2.44E−05 |
| 2 | rs7589832 | 136220571 | Imputed | C/A | 0.194 | 0.256 | 1.90E−04 | 0.70 | 4.25E−05 |
| 2 | rs632632 | 136354686 | Imputed | C/T | 0.274 | 0.350 | 4.67E−05 | 0.70 | 4.85E−05 |
| 2 | rs12619365 | 136114644 | Imputed | T/C | 0.258 | 0.324 | 2.36E−04 | 0.73 | 6.02E−05 |
| 2 | rs2839740 | 136365353 | Imputed | T/G | 0.158 | 0.219 | 9.84E−05 | 0.67 | 6.51E−05 |
| 2 | rs7581814 | 136358063 | Imputed | G/C | 0.158 | 0.219 | 9.64E−05 | 0.67 | 6.57E−05 |

JIA is a complex phenotype comprised of seven subtypes, as defined by the revised ILAR criteria.[3] We analyzed each subtype in our combined dataset of JIA subjects (Table 2) for association signals at rs953387, the non-MHC SNP most significantly associated with all JIA. Five of the seven subtypes showed the same direction of allelic effect, with p values in all but the smallest cohorts ranging from $3.42 \times 10^{-4}$ to $4.09 \times 10^{-3}$ (Table 5); combined analysis of two subtypes, oligoarthritis and RF negative polyarthritis, with an independent cohort from Cincinnati Children's Hospital Medical Center (CCHMC; Cincinnati, Ohio), also showed evidence of association, with a p value of $6.31 \times 10^{-5}$. Of interest, only marginal association of CXCR4 was observed with adult rheumatoid arthritis (RA) in the WTCCC cohort[19] (Table 8). Comparable results were observed in our subjects with rheumatoid factor positive polyarthritis, the JIA subtype most similar to RA, although this remains to be evaluated in a larger study.

To examine whether the SNP genotypes associate with expression levels of CXCR4 mRNA, we explored the Sanger Institute GENe Expression VARiation (Genevar) public database (URLs), which profiles gene expression in immortalized B-lymphocyte samples from HapMap populations.[28] The most significant SNP (rs953387) among six GW-significant SNPs at the CXCR4 locus was assessed in 30 CEU children (see Subjects and Methods, Gene expression). The genotypes of rs953387 associated with expression levels of CXCR4 (p=0.014; FIG. 6). Analysis of an independent dataset of T-cell lines from umbilical cords of 75 individuals of Western European origin[29] also demonstrated association of genotypes of rs1016269 (Table 1) with levels of CXCR4 expression (p=0.0054; FIG. 6). These data suggest that variants in or around CXCR4 regulate mRNA expression of this chemokine receptor.

Discussion

We have identified and replicated common genetic variants on 2q21 that are associated with susceptibility to JIA in a combined sample set of more than 1100 JIA subjects of European ancestry. We propose that susceptibility to JIA is controlled by a number of "master switches", which, like CXCR4, are identifiable by allelic variants in a significantly increased proportion of JIA patients compared to healthy controls. Our data support a role for altered expression of CXCR4 in JIA pathogenesis, although an alternate, testable hypothesis is that these common variants near CXCR4 serve as markers for potentially more rare variants within the coding region of CXCR4. Our results represent, to our knowledge, the first unbiased genome-wide significant association of a common variant with JIA outside of the MHC, and the first genetic demonstration of a possible role for the chemokine receptor, CXCR4, in the pathogenesis of autoimmune disease.

The only previously reported GWAS of JIA was limited by the small size of the discovery cohort (279 samples), coupled with a lack of matching controls and restricted capture of variants by the genotyping platform; the study failed to identify association of any genetic variants with JIA at genome-wide significant levels.[37] A recent candidate gene study identified a number of JIA susceptibility loci in a large case-control cohort;[9] this study—which was not designed as a GWAS—also suffered from restricted variant capture of the genotyping platform (425 candidate non-MHC region SNPs), precluding discovery of novel JIA predisposition factors like the CXCR4 chemokine receptor.

Chemokine receptors are critical regulators of cell migration in immune surveillance, inflammation and development. The G protein-coupled chemokine receptor, CXCR4, is expressed on the surface of T-cells, B-cells, monocytes, neutrophils and dendritic cells (FIG. 7), and is activated exclusively by CXCL12 (also known as stromal-derived-factor-1, SDF-1), a small peptide mediator and potent chemoattractant for leukocytes, including B- and T-cells. CXCR4 and its ligand, CXCL12, have been shown to play a role in B-cell production, myelopoiesis, integrin activation, angiogenesis, and chemotaxis.[38] Intriguingly, the human immunodeficiency virus (HIV-1) has usurped CXCR4's unique CXCL12 binding site, exploiting CXCR4 as a co-receptor in later stages of HIV-1 infection, and CXCR4 antagonists have been explored as treatments for HIV. Binding of CXCR4 to CXCL12 is also proposed to play a role in cancer metastases, and CXCR4 antagonists are under study in human clinical trials for solid and non-solid tumors.[38] Available therapeutic agents targeting the CXCR4-CXCL12 axis for activation or inhibition include plerixafor (AMD3100), recombinant CXCL12, and high-affinity CXCR4 and CXCL12 monoclonal antibodies, some of which are already in use in the clinic but not approved for use in children. The recent report of crystal structures of CXCR4 with small-molecule and cyclic peptide inhibitors[39] provide new opportunities for drug discovery efforts targeting this receptor.

CXCR4 and CXCL12 have been implicated in the pathogenesis of autoimmune diseases.[38,40] In mouse models of autoimmune disease, modulation of CXCR4 alters trafficking of leukocytes to peripheral organs and polarization of regulatory T cells, and accelerates onset of disease.[41,42] This is consistent with our data showing that a risk variant of CXCR4 correlates with decreased expression of CXCR4. An alternate hypothesis is that the effect of low CXCR4 expression is indirect and leads to a compensatory increase of the CXCR4 ligand, CXCL12. Our preliminary data suggest that the risk variant of CXCR4 correlates with increased expression of CXCL12 (data not shown). This is consistent with models of collagen-induced arthritis in which CXCL12 acts as a pro-inflammatory factor in the pathogenesis of inflammatory arthritis,[43,44] and with human studies in which CXCL12 enhances cellular proliferation and cytokine expression by peripheral blood T cells, upregulates expression of cytokines and chemokines by fibroblast-like synoviocytes from patients with RA,[45] and mediates lymphocyte ingress into RA synovial tissue, synovial neovascularisation, and osteoclastogenesis.[46]

Our results indicate that gene variants at the CXCR4 locus predispose to the development of JIA. We have uncovered common tagging SNPs that confer strong effects on a genome-wide scale and replicate in three independent cohorts of JIA patients. The extensive literature surrounding the biology of CXCR4 and CXCL12 in health and disease and the ready availability of targeted therapeutic agents make CXCR4 a particularly attractive candidate for further investigation of its pathogenic role and therapeutic potential in JIA and other autoimmune diseases affecting children.

Table 12 below provides a list of putative test agents that can be screened in accordance with the present invention for efficacy for the treatment and prevention of JIA.

TABLE 12

| Company | Product | Phase | Description | Indication | MOA | Molecule Type |
|---|---|---|---|---|---|---|
| Ablynx nv (ABLX (EBR)) | ALX0651 | PC | ALX-0651 is a nanobody acts by the inhibition of CXCR4. CXCR4 is a chemokine receptor that plays an important role in cell movement, tumor growth and metastasis. ALX-0651 is being developed as an intravenous formulation for the treatment of cancer. | Cancer | CXC chemokine Receptor 4 (CXCR4) Antagonist | — |
| Genzyme Corporation (GENZ) | AMD070 | II | AMD-070 is a new type of antiretroviral known as HIV entry inhibitor that binds to CXCR4 dhemokine receptors and prevents the relevant HIV strains from entering and infecting the target cells. AMD070 is being developed as oral formulation for the treatment of AIDS/HIV. Note: This product is added upon acquisition of AnorMED Inc. | AIDS/HIV | CXC Chemokine Receptor 4 (CXCR4) Antagonist | — |

TABLE 12-continued

| Company | Product | Phase | Description | Indication | MOA | Molecule Type |
|---|---|---|---|---|---|---|
| Genzyme Corporation (GENZ) | AMD3100 | F | AMD-3100 contains plerixafor, a potential new agent for peripheral blood stem cell transplant in cancer patients. It blocks a specific cellular receptor, known as the CXC4 chemokine receptor, which is present on white blood cells and other immune cells. AMD-3100 was under development for the treatment of AIDS/HIV. Note: This product is added upon acquisition of AnorMED Inc. | AIDS/HIV | CXC Chemokine Receptor 4 (CXCR4) Antagonist | Small |
| Affitech A (AFFI (OMX Nordic Exchange Copenhagen)) | AT009 | PC | AT009 is an antibody that targets CXCR4 and its ligand, SDF-1 (Stromal Derived Factor-1). AT009 is being developed for the treatment of inflammation. | Inflammation | CXC Chemokine Receptor 4 (CXCR4) Antagonist | — |
| Biokine Therapeutics Ltd. (Private) | BKT140 | II | BKT140 is a CXC Chemokine Receptor 4 (CXCR4) antagonist. BKT140 is being developed for the treatment of myeloma and other hematological diseases. | Multiple Myeloma (Myeloma) | CXC Chemokine Receptor 4 (CXCR4) Antagonist | — |
| Daiichi Sankyo Company, Limited (Stock Code Number: 4568 (TYO)) | CS3955 | D | CS-3955 is a CXCR4 (Chemokine Receptor 4) antagonist. It inhibits the binding between HIV and CXCR4. CS-3955 was under development as an oral formulation for the treatment of HIV infection. Note: This product is added upon the merger of Daiichi Pharmaceutical Co., Ltd. with Sankyo Co., Ltd | AIDS/HIV | CXC Chemokine Receptor 4 (CXCR4) Antagonist | — |
| Kureha Corporation (formerly Kureha Chemical Industry Co., Ltd.) (Stock Code Number: 4023 (TYO)) | CS3955 | D | CS-3955 is a CXCR4 (Chemokine Receptor 4) antagonist. It inhibits the binding between HIV and CXCR4. CS-3955 was under development as an oral formulation for the treatment of HIV infection. | AIDS/HIV | CXC Chemokine Receptor 4 (CXCR4) Antagonist | — |
| British Canadian BioSciences Corp. (BCBC) (Private) | CTCE0214 | I | CTCE-0214 is an analog of SDF-1 and agonist of the SDF-1 receptor, CXCR4. It mobilizes blood and progenitor cells and enhances the survival and expansion of cord blood cells. It rapidly increases the number of stem cells and white blood cells (WBC) for patients with chemotherapy induced Neutropenia. CTCE-0214 is being developed as a subcutaneous formulation for the treatment of neutropenia. | Neutropenia | CXC Chemokine Receptor 4 (CXCR4) Antagonist | — |
| British Canadian BioSciences Corp. (BCBC) (Private) | CTCE0324 | PC | CTCE-0324 is a peptide agonist that is an analog of SDF-1. It binds to CXCR4 and induces a host of cellular responses, leading to the development of tube-like structures and sprouting of new blood vessels from existing ones. CTCE-0324 is being developed as an injection for the treatment of vascular disease by inducing the formation of new blood vessels to circumvent existing narrowed blood vessels. | Peripheral Vascular Disease | CXC Chemokine Receptor 4 (CXCR4) Agonist | — |
| British Canadian BioSciences Corp. (BCBC) (Private) | CTCE9908 | PC | CTCE-9908 is an analog of stromal cell-derived factor 1 (SDF-1), acts as a competitive antagonist at CXCR4 receptors and inhibits the metastasis of cancer cells. It destroys the primary tumors and delays the occurrence of secondary tumors. CTCE-9908 is being developed as an injection for the treatment of cancer (ovarian cancer and prostate cancer). | Cancer | CXC Chemokine Receptor 4 (CXCR4) Antagonist | — |
| British Canadian BioSciences Corp. (BCBC) (Private) | CTCE9908 | II | CTCE-9908, a small protein is an analog of stromal cell-derived factor 1 (SDF-1), acts as a competitive antagonist at CXCR4 receptors and inhibits the metastasis of cancer cells. It destroys the primary tumors and delays the occurrence of secondary tumors. CTCE-9908 is being developed as an injection of the treatment of liver cancer. | Liver Cancer | CXC Chemokine Receptor 4 (CXCR4) Antagonist | — |
| ChemoCentryx, Inc. (Private) | CXCR4 Antagonist CHEMOCENTRYX | PC | CXCR4 antagonist is a high potency small module antagonist of chemokine receptor target CXCR4, which is expressed by both cancerous and non-cancerous cell types. CXCR4 antagonist is being developed for the treatment of inflammatory disorders. | Inflammation (Inflammatory Disorders) | CXC Chemokine Receptor 4 (CXCR4) Antagonist | Small |
| Shanghai Targetdrug Ltd. (Private) | CXCR4 antagonist TARGETDRUG | NA | CXCR4 antagonist is a human chemokine receptor blocker. It blocks T cell migration in the inflamed rheumatoid arthritis synovium. It is being developed for the treatment of rheumatoid arthritis. | Rheumatoid Arthritis | CXC Chemokine Receptor 4 (CXCR4) Antagonist | — |

TABLE 12-continued

| Company | Product | Phase | Description | Indication | MOA | Molecule Type |
|---|---|---|---|---|---|---|
| Shanghai Targetdrug Ltd. (Private) | CXCR4 antagonist TARGETDRUG | NA | CXCR4 antagonist is a human chemokine receptor blocker. It decreases CD4+ and CD8+ T-cell recruitment and airway hyperresponsiveness and reduces the airway inflammation in It is being developed for the treatment of asthma. | Asthma | CXC Chemokine Receptor 4 (CXCR4) Antagonist | — |
| Northwest Biotherapeutics Inc (NWBO) | CXCR4 antibody NORTHWEST | PC | CXCR4 antibody (CXC chemokine receptor 4 monoclonal antibody) works by inhibiting the tumor growth and induces cell death (apoptosis). It also blocks the movement or chemotaxis and the invasion of cancer cells through other tissues. CXCR4 antibody is being developed for the treatment of cancer. | Cancer | CXC Chemokine Receptor 4 (CXCR4) Antagonist | Large |
| Genzyme Corporation (GENZ) | CXCR4 Inhibitor GENZYME | D | CXCR4 is a chemokine receptor which is present on white blood cells and plays a key regulatory role in trafficking and homing of cells involved in the immune system. Chemokine inhibitors block chemokine receptors, and prevent the chemotaxis from occurring. CXCR4 Inhibitor was under development for the treatment of cancer. Note: This product is added upon acquisition of AnorMED Inc. | Cancer | CXC Chemokine Receptor 4 (CXCR4) Antagonist | — |
| GlaxoSmithKline plc (GSK (LON)) | GSK812397 | NA | GSK812397 is a noncompetetive CXCR4 (CXC chemokine receptor) antagonist that acts by inhibiting the cellular entry of X4-tropic strains of HIV-1 and is being developed for the treatment of HIV-1 infections. | AIDS/HIV (HIV-1 Infections) | CXC Chemokine Receptor 4 (CXCR4) Antagonist | — |
| Kureha Corporation (formerly Kureha Chemical Industry Co., Ltd.) (Stock Code Number: 4023 (TYO)) | KRH3140 | D | KRH-3140 is an antiviral drug interferes with HIV-1 entry into T cells by antagonizing CXC chemokine receptor 4. KRH-3140 was under development as oral formulation for the treatment of HIV/AIDS. | AIDS/HIV | CXC Chemokine Receptor 4 (CXCR4) Antagonist | — |
| Kureha Corporation (formerly Kureha Chemical Industry Co., Ltd.) (Stock Code Number: 4023 (TYO)) | KRH3955 | D | KRH-3955 is an antiviral drug, which interferes with HIV-1 entry into T cells by antagonizing CXC chemokine receptor 4. KRH-3955 was under development as oral formulation for the treatment of HIV/AIDS. | AIDS/HIV | CXC Chemokine Receptor 4 (CXCR4) Antagonist | — |
| Bristol-Myers Squibb Company (BMY) | MDX1338 | I | MDX-1338 acts on chemokine receptor CXCR4, expressed on tumor cells and induce apoptosis and inhibit proliferation, angiogenesis and metastasis of tumor cells. MDX-1338 is being developed for the treatment of relapsed/refractory acute myelogenous leukemia. Note: This product is added upon the acquisition of Medarex Inc. | Acute Myelogenous Leukemia (Relapsed/ Refractory Acute Myelogenous Leukemia) | CXC Chemokine Receptor 4 (CXCR4) Antagonist | — |
| Genzyme Corporation (GENZ) | Mozobil | PC | Mozobil contains plerixafor, a novel hematopoietic stem cell (HSC) mobilizer. It blocks a specific cellular receptor, known as the CXCR4 chemokine receptor, triggering the movement of stem cells out of the bone marrow and into the circulating blood. Mozobl is being developed as subcutaneous injection for the treatment of solid organ transplant/autoimmune diseases. Note: This product is added upon acqistion of AnorMED Inc. | Autoimmune Diseases | CXC Chemokine Receptor 4 (CXCR4) Antagonist | Small |
| Genzyme Corporation (GENZ) | Mozobil | PC | Mozobil contains plerixafor, a novel hematopoietic stem cell (HSC) mobilizer. It blocks a specific cellular receptor, known as the CXCR4 chemokine receptor, triggering the movement of stem cells out of the bone marrow and into the circulating blood. Mozobil is being developed for the treatment of ischemic renal disease. | Kidney Disease (Ischemic Renal Disease) | CXC Chemokine Receptor 4 (CXCR4) Antagonist | Small |
| Genzyme Corporation (GENZ) | Mozobil | M | Mozobil is a novel hematopoietic stem cell (HSC) mobilizer. It blocks a specific cellular receptor, known as the CXCR4 chemokine receptor, triggering the movement of stem cells out of the bone marrow and into the circulating blood. Mozobil injection is intended to be used in combination with granulocyte-colony stimulating factor (G-CSF) to mobilize hematopoietic stem | Transplantation (Stem Cell Transplantation in Cancer) | CXC Chemokine Receptor 4 (CXCR4) Antagonist | Small |

TABLE 12-continued

| Company | Product | Phase | Description | Indication | MOA | Molecule Type |
|---|---|---|---|---|---|---|
| | | | cells to the bloodstream for collection and subsequent autologous transplantation in patients with non-Hodgkin's lymphoma (NHL) and multiple myeloma (MM). It is available as subcutaneous injection (20 mg/ml) Note: This product is added upon acquisition of AnorMED Inc. | | | |
| Genzyme Corporation (GENZ) | Mozobil | D | Mozobil is a novel stem cell mobilizer, contains plerixafor as active ingredient. It acts by blocking a specific cellular receptor, known as the CXCR4 chemokine receptor, triggering the movement of stem cells out of the bone marrow and into the circulating blood. Mozobil was under development as subcutaneous injection for stem cell transplantation in patients who have suffered heart attacks. Note: This product is added upon acquisition of AnorMED Inc. | Transplantation (Stem Cell Transplantation for Heart Tissue Repair) | CXC Chemokine Receptor 4 (CXCR4) Antagonist | Small |
| Genzyme Corporation (GENZ) | Mozobil with Mitoxantrone, Etoposide and Cytarabine | II | Mozobil is a novel stem cell mobilizer, contains plerixafor as active ingredient. It acts by blocking a specific cellular receptor, known as the CXCR4 chemokine receptor, triggering the movement of stem cells out of the bone marrow and into the circulating blood. Mozobil (intravenous) in combination with Mitoxantrone (intravenous), Etoposide (intravenous) and Cytarabine (intravenous) is being developed as subcutaneous injection for tumor sensitization in relapsed or refractory acute myeloid leukemia. Note: This product is added upon acquisition of AnorMED Inc. | Acute Myelogenous Leukemia (Relapsed or Refractory Acute Myelogenous Leukemia) | CXC Chemokine Receptor 4 (CXCR4) Antagonist | — |
| Genzyme Corporation (GENZ) | Mozobil with Rituximab | II | Mozobil contains plerixafor that acts by blocking a specific cellular receptor, known as the CXCR4 chemokine receptor, triggering the movement of stem cells out of the bone marrow and into the circulating blood. Rituximab is a genetically engineered chimeric monoclonal antibody that targets a receptor called CD20 found on some B-cells. It induces lysis through several proposed mechanisms, work with elements of the human immune system to kill CD20+ B cells through antibody-dependent toxicity (ADCC) and complement-dependent cytotoxicity (CDC). Mozobil (subcutaneous), Rituximab combination is being developed for the treatment of chronic lymphocytic leukemia or small lymphocytic lymphoma. | Chronic Lymphocytic Leukemia | CXC Chemokine Receptor 4 (CXCR4) Antagonist; Membrane-Spanning 4-Domains, Subfamily A, Member 1 (MS4A1) Inhibitor | — |
| Genzyme Corporation (GENZ) | Mozobil with Velcade | II | Mozobil contains plerixafor that acts by blocking a specific cellular receptor, known as the CXCR4 chemokine receptor, triggering the movement of stem cells out of the bone marrow and into the circulating blood. Velcade contains bortezomib. Bortezomib is a proteasome inhibitor. Proteasomes are enzyme complexes which are present in all cells which break down intracellular proteins in a regulated manner in both healthy and cancerous cells. Inhibition of the proteasome prevents the regulated breakdown of these intracellular proteins, thereby interfering with many of these varied functions. This disruption of essential pathways in cancer cells can lead to cell death and inhibit tumor growth. Mozobil (subcutaneous) in combination with Velcade (bortezomib) (intravenous) is being developed for the treatment of relapsed or relapsed/refractory multiple myeloma. | Multiple Myeloma (Relapsed or Relapsed/ Refractory Multiple Myeloma) | 26S Proteasome Inhibitor; CXC Chemokine Receptor 4 (CXCR4) Antagonist | — |
| NeED pharma (Private) | ND401 | NA | ND401 is a compound that blocks viral infection by inhibition of both CC Chemokine receptors (CCR5) and CXC Chemokine receptor (CXCR4) co-receptors. ND401 is being developed for the treatment of HIV Infection. | AIDS/HIV | CC Chemokine Receptor 5 (CCR5) Antagonist; CXC Chemokine Receotor 4 (CXCR4) Antagonist | — |

TABLE 12-continued

| Company | Product | Phase | Description | Indication | MOA | Molecule Type |
|---|---|---|---|---|---|---|
| Osprey Pharmaceuticals USA (OPUS) (Private) | OPLCXCL12LPM | NA | OPL-CXCL12-LPM, a leukocyte population modulator is a highly potent inhibitor of CXCL12-CXCR4 signaling pathway. Leukocyte population modulator is a recombinant fusion protein comprised of a receptor-binding chemokine moiety connected to a cellular toxin via peptide linker. OPL-CXCL12-LPM is being developed based on LPM platform technology for the treatment of ovarian cancer. | Ovarian Cancer | CXC Chemokine Receptor 4 (CXCR4) Antagonist | — |
| Polyphor Ltd (Private) | POL6326 | PC | POL-6326 is a potent, selective and reversible CXCR4 inhibitor which is based on Protein Epitope Mimetics (PEM) technology. POL-6326 is being developed for the regeneration of tissue in wound healing process. | Wounds (Wound Healing) | CXC Chemokine Receptor 4 (CXCR4) Antagonist | — |
| Polyphor Ltd (Private) | POL6326 | PC | POL-6326 is a potent, selective and reversible CXCR4 inhibitor. It is based on Protein Epitope Mimetics (PEM) technology. POL-6326 is being developed for the treatment of inflammation. | Inflammation | CXC Chemokine Receptor 4 (CXCR4) Antagonist | — |
| Polyphor Ltd (Private) | POL6326 | PC | POL-6326 is a potent, selective and reversible CXCR4 inhibitor. It is based on Protein Epitope Mimetics (PEM) technology. POL-6326 is being developed for the treatment of inflammation. | Leukemia | CXC Chemokine Receptor 4 (CXCR4) Antagonist | — |
| Polyphor Ltd (Private) | POL6326 | II | POL-6326 is a potent, selective and reversible CXCR4 inhibitor which is based on Protein Epitope Mimetics (PEM) technology. Blockade of the CXCR4 receptor mobilizes hematopoietic stem cell from the bone marrow into the blood stream where they can be harvested for transplant supporting the treatment of blood or bone marrow diseases. POL-6326 is being developed as intravenous and subcutaneous formulations for the treatment of transplantation. | Transplantation (Hematopoietic Stem Cell Transplantation) | CXC Chemokine Receptor 4 (CXCR4) Antagonist | — |
| Angioblast Systems, Inc. (Private) | SDF-1 ANGIOBLAST | PC | SDF-1 (Stromal derived factor 1) is chemically synthesized short peptide based product known as chemokines, which is a cytokine and antigen receptor inhibitor. It acts by inducing the stem cell migration. Stromal derived factor 1 is being developed for the treatment of congestive heart failure and myocardial infraction. | Cardiovascular Disease | CXC Chemokine Receptor 4 (CXCR4) Agonist | — |
| Samaritan Pharmaceuticals Inc (SPHC) | SP01A | III | SP-01A is an oral HIV entry inhibitor drug. It cripples HIV's ability to enter cells by blocking the proteins on human T Cells that would, otherwise, facilitate HIV's entry into those cells. It reduces intracellular cholesterol and corticosteroid biosynthesis, which causes the inability of lipid rafts in the cellular membrane to organize, ultimately preventing fusion of an HIV receptor and both the CCR5 and CXCR4 cellular receptors. SP-01A is being developed for the treatment of AIDS/HIV infection. | AIDS/HIV | CC Chemokine Receptor 5 (CCR5) Antagonist; CXC Chemokine Receptor 4 (CXCR4) Antagonist | — |
| TaiGen Biotechnology Co., Ltd. (Private) | TG0054 | PC | TG-0054 is a potent and selective chemokine receptor 4 antagonist that effectively mobilizes bone marrow stem/progenitor cells into peripheral circulation. These stem/progenitor cells can perform tissue and vasculature repair. TG-0054 is being developed for the treatment of eye diseases like age related macular degeneration and diabetic retinopathy | Eye Diseases (General) (Eye Diseases) | CXC Chemokine Receptor 4 (CXCR4) Antagonist | — |
| TaiGen Biotechnology Co., Ltd. (Private) | TG0054 | I | TG-0054 is a potent and selective chemokine receptor 4 antagonist that effectively mobilizes bone marrow stem/progenitor cells into peripheral circulation. These stem/progenitor cells can perform tissue and vasculature repair. TG-0054 is being developed as an intravenous formulation for the treatment of cardiovascular diseases like intermittent claudication, myocardial infarction and non-hemorrhagic stroke. | Cardiovascular Dieases | CXC Chemokine Receptor 4 (CXCR4) Antagonist | — |

TABLE 12-continued

| Company | Product | Phase | Description | Indication | MOA | Molecule Type |
|---|---|---|---|---|---|---|
| TaiGen Biotechnology Co., Ltd. (Private) | TG0054 | II | TG0054 is a potent and selective chemokine receptor 4 (CXCR4) antagonist that effectively mobilizes bone marrow stem/progenitor cells into peripheral circulation. These stem/progenitor cells can perform tissue and vasculature repair. TG0054 is being developed as an intravenous formulation for stem cell transplantation in cancer patients with multiple myeloma, non-Hodgkin lymphoma and Hodgkin disease patients. | Cancer (Stem Cell Transplantation In Cancer Patients) | CXC Chemokine Receptor 4 (CXCR4) Antagonist | — |

Example 2

Through exome sequencing of the CXCR4 gene in 432 JIA cases using next-generation sequencing technology, we have identified 3 nonsynonymous mutations (nsSNVs) and one stop/gain mutation (stop codon) of which only one is found to exist in one individual in a public sequencing database of 6,500 subjects. All 4 variants are otherwise absent in our control cohort as well as the 1000 genome project.

Moreover, in a nsSNV burden analysis of our case cohort in comparison with controls and public databases combined of over 7,500 subjects, we observed that the rare variant burden of nsSNVs that are predicted by SIFT and PolyPhren scores to be highly damaging to the function of the CXCR4 protein are over 4× more common in the JIA patients compared to controls (P=0.0175; OR=4.661764 with 95% CI [1.121435 14.721356]).

These results suggest that these mutations, all of which are predicted to be pathogenic to the function of the CXCR4 gene, are highly relevant to the pathogenesis of JIA and strongly support CXCR4 as an important disease gene and therapeutic target in JIA.

| Gene | Exonic Function | Amino Acid Change |
|---|---|---|
| CXCR4 | nonsynonymous SNV | NM_001008540:c.C1049A:p.S350Y |
| CXCR4 | nonsynonymous SNV | NM_001008540:c.A169C:p.I57L* |
| CXCR4 | nonsynonymous SNV | NM_001008540:c.C19G:p.L7V |
| CXCR4 | stopgain SNV | (NM_001008540:c.T14A:p.L5X stop codon) |

*present in one control subject of over 7,500 and this mutation is the least detrimental of the four mutations identified.

The information herein above can be applied clinically to patients for diagnosing an increased susceptibility for developing JIA, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing JIA. This can occur after a patient arrives in the clinic; the patient has blood drawn, and using the diagnostic methods described herein, a clinician can detect one or more indicative SNPs or mutations described in the present application. The information obtained from the patient sample, which can optionally be amplified prior to assessment, will be used to diagnose a patient with an increased or decreased susceptibility for developing JIA. Kits for performing the diagnostic method of the invention are also provided herein. Such kits comprise a microarray comprising at least one, two, three, four, five, six or all of the SNPs provided herein in and the necessary reagents for assessing the patient samples as described above.

The invention also provides a method of treating JIA in a patient determined to have at least one prescribed single nucleotide polymorphism indicative of the presence of JIA, by administering to the patient a therapeutically effective amount of at least one member of the agents listed in Table 12. This method provides a test and treat paradigm, whereby a patient's genetic profile is used to personalize treatment with therapeutics targeted towards specific immunological defects found in individuals exhibiting JIA. Such a test and treat model may benefit up to 50% of patients with JIA with greater efficacy and fewer side effects than non-personalized treatment.

The identity of SNPs and mutations present in the CXCR4 gene and the patient results will indicate which variants are present, and will identify those that possess an altered risk for developing JIA. The information provided herein allows for therapeutic intervention at earlier times in disease progression that previously possible. Also as described herein above, SNP containing CXCR4 genes involved in JIA pathogenesis have been identified which provide novel targets for the development of new therapeutic agents efficacious for the treatment of JIA.

Web Resources (URLs)

The URLs for data presented herein are as follows:

JIA Calculator, on the world wide web at jra-research.org/JIAcalc/index.php
PLINK, on the world wide web at pngu.mgh.harvard.edu/~purcell/plink/
WGAViewer, on the world wide web at people.genome.duke.edu/~dg48/GAViewer/
MACH, on the world wide web at sph.umich.edu/csg/abecasis/MaCH/index.html
Metal, on the world wide web at sph.umich.edu/csg/abecasis/Metal/index.html
MOOSE, on the world wide web at jama.ama-assn.org/cgi/content/full/283/15/2008
Genevar, on the world wide web at sanger.ac.uk/resources/software/genevar/
HapMap, on the world wide web at hapmap.ncbi.nlm.nih.gov/
Quanto, on the world wide web at hydra.usc.edu/gxe/

REFERENCES

1. Hayward, K., Wallace, C. A. (2009). Recent developments in anti-rheumatic drugs in pediatrics: treatment of juvenile idiopathic arthritis. Arthritis Res. Ther. 11, 216.
2. Aletaha, D., Neogi, T., Silman, A. J., Funovits, J., Felson, D. T., Bingham, C. O. 3rd, Birnbaum, N. S., Burmester, G. R., Bykerk, V. P., Cohen, M. D., et al. (2010). Rheumatoid arthritis classification criteria: an American College of Rheumatology/European League Against Rheumatism collaborative initiative. Arthritis Rheum. 62, 2569-2581.
3. Petty, R. E., Southwood, T. R., Manners, P., Baum, J., Glass, D. N., Goldenberg, J., He, X., Maldonado-Cocco, J., Orozco-Alcala, J., Prieur, A. M., et al. (2001). International League of Associations for Rheumatology classification of juvenile idiopathic arthritis: second revision, Edmonton. J. Rheumatol. 31, 390-392.
4. Peterson, L. S., Mason, T., Nelson, A. M., O'Fallon, W. M., Gabriel, S. E. (1997). Psychosocial outcomes and health status of adults who have had juvenile rheumatoid arthritis: a controlled, population-based study. Arthritis Rheum. 40, 2235-2240.
5. Ellis, J. A., Munro, J. E., Ponsonby, A. L. (2010). Possible environmental determinants of juvenile idiopathic arthritis. Rheumatology (Oxford). 49, 411-425.
6. Woo, P., Colbert, R. A. (2009). An overview of genetics of pediatric rheumatic diseases. Best Pract. Res. Clin. Rheumatol. 23, 589-597.
7. Hollenbach, J. A., Thompson, S. D., Bugawan, T. L., Ryan, M., Sudman, M., Marion, M., Langefeld, C. D., Thomson, G., Erlich, H. A., Glass, D. N. (2010). Juvenile idiopathic arthritis and HLA class I and class II interactions and age-at-onset effects. Arthritis Rheum. 62, 1781-1791.
8. Prahalad, S., Shear, E. S., Thompson, S. D., Giannini, E. H., Glass, D. N. (2002). Increased prevalence of familial autoimmunity in simplex and multiplex families with juvenile rheumatoid arthritis. Arthritis Rheum. 46, 1851-1856.
9. Thompson, S. D., Sudman, M., Ramos, P. S., Marion, M. C., Ryan, M., Tsoras, M., Weiler, T., Wagner, M., Keddache, M., Haas, J. P., et al. (2010). The susceptibility loci juvenile idiopathic arthritis shares with other autoimmune diseases extend to PTPN2, COG6, and ANGPT1. Arthritis Rheum. 62, 3265-3276.
10. Hinks, A., Eyre, S., Ke, X., Barton, A., Martin, P., Flynn, E., Packham, J., Worthington, J., Childhood Arthritis Prospective Study, UKRAG Consortium, et al. (2010). Association of the AFF3 gene and IL2/IL21 gene region with juvenile idiopathic arthritis. Genes Immun 11, 194-198.
11. Prahalad, S., Hansen, S., Whiting, A., Guthery, S. L., Clifford, B., McNally, B., Zeft, A. S., Bohnsack, J. F., Jorde, L. B. (2009). Variants in TNFAIP3, STAT4, and C12orf30 loci associated with multiple autoimmune diseases are also associated with juvenile idiopathic arthritis. Arthritis Rheum. 60, 2124-2130.
12. Behrens, E. M., Finkel, T. H., Bradfield, J. P., Kim, C. E., Linton, L., Casalunovo, T., Frackelton, E. C., Santa, E., Otieno, F. G., Glessner, J. T., et al. (2001). Association of the TRAF1-05 locus on chromosome 9 with juvenile idiopathic arthritis. Arthritis Rheum. 58, 2206-2207.
13. Zhernakova, A., van Diemen, C. C., Wijmenga, C. (2009). Detecting shared pathogenesis from the shared genetics of immune-related diseases. Nat. Rev. Genet. 10, 43-55.
14. Behrens, E. M., Beukelman, T., Gallo, L., Spangler, J., Rosenkranz, M., Arkachaisri, T., Ayala, R., Groh, B., Finkel, T. H., Cron, R. Q. (2008). Evaluation of the presentation of systemic onset juvenile rheumatoid arthritis: data from the Pennsylvania Systemic Onset Juvenile Arthritis Registry (PASOJAR). J. Rheumatol. 35, 343-348.
15. Wise, C. A., Bennett, L. B., Pascual, V., Gillum, J. D., Bowcock, A. M. (2000). Localization of a gene for familial recurrent arthritis. Arthritis Rheum. 43, 2041-2045.
16. Becker, M. L., Gaedigk, R., van Haandel, L., Thomas, B., Lasky, A., Hoeltzel, M., Dai, H., Stobaugh, J., Leeder, J. S. (2011). The effect of genotype on methotrexate polyglutamate variability in juvenile idiopathic arthritis and association with drug response. Arthritis Rheum. 63, 276-285.
17. Eike, M. C., Nordang, G. B., Karlsen, T. H., Boberg, K. M., Vatn, M. H., IBSEN study group, Dahl-Jørgensen, K., Rønningen, K. S., Joner, G., Flan), B., et al. (2008). The FCRL3-169T>C polymorphism is associated with rheumatoid arthritis and shows suggestive evidence of involvement with juvenile idiopathic arthritis in a Scandinavian panel of autoimmune diseases. Ann. Rheum. Dis. 67, 1287-1291.
18. Purcell, S., Neale, B., Todd-Brown, K., Thomas, L., Ferreira, M. A., Bender, D., Mailer, J., Sklar, P., de Bakker, P. I., Daly, M. J., et al. (2007). PLINK: a tool set for whole-genome association and population-based linkage analyses. Am. J. Hum. Genet. 81, 559-575.
19. Wellcome Trust Case Control Consortium. (2007). Genome-wide association study of 14,000 cases of seven common diseases and 3,000 shared controls. Nature. 447, 661-678.
20. Shi, J., Levinson, D. F., Duan, J., Sanders, A. R., Zheng, Y., Pe'er, I., Dudbridge, F., Holmans, P. A., Whittemore, A. S., Mowry, B. J., et al. (2009). Common variants on chromosome 6p22.1 are associated with schizophrenia. Nature. 460, 753-757.
21. Hattersley, A. T., McCarthy, M. I. (2005). What makes a good genetic association study? Lancet. 366, 1315-1323.
22. McCarthy, M. I., Abecasis, G. R., Cardon, L. R., Goldstein, D. B., Little, J., Ioannidis, J. P., Hirschhorn, J. N. (2008). Genome-wide association studies for complex traits: consensus, uncertainty and challenges. Nat. Rev. Genet. 9, 356-369.
23. Little, J., Higgins, J. P., Ioannidis, J. P., Moher, D., Gagnon, F., von Elm, E., Khoury, M. J., Cohen, B., Davey-Smith, G., Grimshaw, J., et al. (2009). Strengthening the reporting of genetic association studies (STREGA): an extension of the STROBE statement. Hum. Genet. 125, 131-151.
24. Kugathasan, S., Baldassano, R. N., Bradfield, J. P., Sleiman, P. M., Imielinski, M., Guthery, S. L., Cucchiara, S., Kim, C E, Frackelton, E. C., Annaiah, K., et al. (2008). Loci on 20q13 and 21q22 are associated with pediatric-onset inflammatory bowel disease. Nat. Genet. 40, 1211-1215.
25. Li, Y., Willer, C., Sanna, S., Abecasis, G. (2009). Genotype imputation. Annu. Rev. Genomics Hum. Genet. 10, 387-406.
26. Wei, Z., Wang, K., Qu, H. Q., Zhang, H., Bradfield, J., Kim, C., Frackleton, E., Hou, C., Glessner, J. T., Chiavacci, R., et al. (2009). From disease association to risk assessment: an optimistic view from genome-wide association studies on type 1 diabetes. PLoS Genet. 5, e1000678.
27. Stranger, B. E., Forrest, M. S., Dunning, M., Ingle, C. E., Beazley, C., Thorne, N., Redon, R., Bird, C. P., de Grassi, A., Lee, C., et al. (2007). Relative impact of nucleotide and copy number variation on gene expression phenotypes. Science. 315, 848-853.

28. Yang, T. P., Beazley, C., Montgomery, S. B., Dimas, A. S., Gutierrez-Arcelus, M., Stranger, B. E., Deloukis, P., Dermitzakis, E. T. (2010). Genevar: a database and Java application for the analysis and visualization of SNP-gene associations in eQTL studies. Bioinformatics. 26, 2474-2476.
29. Dimas, A. S., Deutsch, S., Stranger, B. E., Montgomery, S. B., Borel, C., Attar-Cohen, H., Ingle, C., Beazley, C., Gutierrez Arcelus, M., Sekowska, M., et al. (2009). Common regulatory variation impacts gene expression in a cell type dependent manner. Science. 325, 1246-1250.
30. Stranger, B. E., Forrest, M. S., Clark, A. G., Minichiello, M. J., Deutsch, S., Lyle, R., Hunt, S., Kahl, B., Antonarakis, S. E., Tavaré, S., et al. (2005). Genome-wide associations of gene expression variation in humans. PLoS Genet. 1, e78.
31. Stranger, B. E., Nica, A. C., Forrest, M. S., Dimas, A., Bird, C. P., Beazley, C., Ingle, C. E., Dunning, M., Flicek, P., Koller, D., et al. (2007). Population genomics of human gene expression. Nat. Genet. 39, 1217-1224.
32. Kuhn, K., Baker, S. C., Chudin, E., Lieu, M. H., Oeser, S., Bennett, H., Rigault, P., Barker, D., McDaniel, T. K., Chee, M. S. (2004). A novel, high-performance random array platform for quantitative gene expression profiling. Genome Res. 14, 2347-2356.
33. Bolstad, B. M., Irizarry, R. A., Astrand, M., Speed, T. P. (2003). A comparison of normalization methods for high density oligonucleotide array data based on variance and bias. Bioinformatics. 19, 185-193.
34. Devlin, B., Roeder, K. (1999). Genomic control for association studies. Biometrics. 55, 997-1004.
35. Conneely, K. N., Boehnke, M. (2007). So many correlated tests, so little time! Rapid adjustment of p-values for multiple correlated tests. Am. J. Hum. Genet. 81, 1158-1168.
36. Willer, C. J., Li, Y., Abecasis, G. R. (2010). METAL: fast and efficient meta-analysis of genomewide association scans. Bioinformatics. 26, 2190-2191.
37. Hinks, A., Barton, A., Shephard, N., Eyre, S., Bowes, J., Cargill, M., Wang, E., Ke, X., Kennedy, G. C., John, S., et al. (2009). Identification of a novel susceptibility locus for juvenile idiopathic arthritis by genome-wide association analysis. Arthritis Rheum. 60, 258-263.
38. Chong, B. F., Mohan, C. (2009). Targeting the CXCR4/CXCL12 axis in systemic lupus erythematosus. Expert Opin. Ther. Targets. 13, 1147-1153.
39. Wu, B., Chien, E. Y., Mol, C. D., Fenalti, G., Liu, W., Katritch, V., Abagyan, R., Brooun, A., Wells, P., Bi, F. C., et al. (2010). Structures of the CXCR4 chemokine GPCR with small-molecule and cyclic peptide antagonists. Science. 330, 1066-1071.
40. Koch, A. E. (2005). Chemokines and their receptors in rheumatoid arthritis: future targets? Arthritis Rheum. 52, 710-721.
41. Aboumrad, E., Madec, A. M., Thivolet, C. (2007). The CXCR4/CXCL12 (SDF-1) signalling pathway protects non-obese diabetic mouse from autoimmune diabetes. Clin. Exp. Immunol. 148, 432-439.
42. Meiron, M., Zohar, Y., Anunu, R., Wildbaum, G., Karin, N. (2008). CXCL12 (SDF-1alpha) suppresses ongoing experimental autoimmune encephalomyelitis by selecting antigen-specific regulatory T cells. J. Exp. Med. 205, 2643-2655.
43. De Klerck, B., Geboes, L., Hatse, S., Kelchtermans, H., Meyvis, Y., Vermeire, K., Bridger, G., Billiau, A., Schols, D., Matthys, P. (2005). Pro-inflammatory properties of stromal cell-derived factor-1 (CXCL12) in collagen-induced arthritis. Arthritis Res. Ther. 7, R1208-20.
44. Bradfield, P. F., Amft, N., Vernon-Wilson, E., Exley, A. E., Parsonage, G., Rainger, G. E., Nash, G. B., Thomas, A. M., Simmons, D. L., Salmon, M., et al. (2003). Rheumatoid fibroblast-like synoviocytes overexpress the chemokine stromal cell-derived factor 1 (CXCL12), which supports distinct patterns and rates of CD4+ and CD8+ T cell migration within synovial tissue. Arthritis Rheum. 48, 2472-2482.
45. Nanki, T., Nagasaka, K., Hayashida, K., Saita, Y., Miyasaka, N. (2001). Chemokines regulate 11-6 and IL-8 production by fibroblast-like synoviocytes from patients with rheumatoid arthritis. J. Immunol. 167, 5381-5385.
46. Nanki, T., Hayashida, K., El-Gabalawy, H. S., Suson, S., Shi, K., Girschick, H. J., Yavuz, S., Lipsky, P. E. (2000). Stromal cell-derived factor-1-CXC chemokine receptor 4 interactions play a central role in CD4+ T cell accumulation in rheumatoid arthritis synovium. J. Immunol. 165, 6590-6898.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:

1. A method for the treatment of Juvenile Idiopathic Arthritis (JIA) in a human subject in need thereof comprising;
    a) testing a DNA sample from said subject for the presence of:
        i) JIA-associated single nucleotide polymorphisms (SNPs) selected from:
            1. major allele T at rs953387;
            2. major allele C at rs1123848;
            3. major allele A at rs4954564;
            4. major allele G at rs1016269; and
        ii) JIA-associated single nucleotide variations (SNVs) selected from:
            1. a C to A substitution at nucleotide position 1049 of the CXCR4 cDNA which results in an S to Y amino acid change at amino acid position 350 of the CXCR4 protein;
            2. an A to C substitution at nucleotide position 169 of the CXCR4 cDNA which results in an I to L amino acid change at position 57 of the CXCR4 protein;
            3. a C to G substitution at nucleotide position 19 of the CXCR4 cDNA which results in a L to V amino acid change at amino acid position 7 of the CXCR4 protein; and
            4. a T to A substitution at nucleotide position 14 of the CXCR4 cDNA which results in the presence of a stop codon in place of amino acid L at position 5 of the CXRC4 protein;
    b) detecting the presence of any of said SNV and/or SNP as indicative that said subject has an increased risk for developing JIA; and
    c) administering an effective amount of an anti-CXCR4 antibody to the subject.

2. The method of claim 1, wherein said anti-CXCR4 antibody modulates the inflammatory process.

3. The method of claim 1, wherein said anti-CXCR4 antibody modulates cytokine release.

* * * * *